(12) United States Patent
Lee et al.

(10) Patent No.: US 10,860,850 B2
(45) Date of Patent: Dec. 8, 2020

(54) METHOD OF RECOGNITION BASED ON IRIS RECOGNITION AND ELECTRONIC DEVICE SUPPORTING THE SAME

(71) Applicant: Samsung Electronics Co., Ltd., Suwon-si (KR)

(72) Inventors: Kwang Hyun Lee, Suwon-si (KR); Ju Woan Yoo, Anyang-si (KR); Hee Jun Lee, Seoul (KR); Dae Kyu Shin, Suwon-si (KR); Ji Yoon Park, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 145 days.

(21) Appl. No.: 15/895,582

(22) Filed: Feb. 13, 2018

(65) Prior Publication Data
US 2018/0276465 A1 Sep. 27, 2018

(30) Foreign Application Priority Data
Mar. 27, 2017 (KR) .................. 10-2017-0038207

(51) Int. Cl.
*G06K 9/00* (2006.01)
*A61B 5/1171* (2016.01)
(Continued)

(52) U.S. Cl.
CPC ........ *G06K 9/00604* (2013.01); *A61B 5/1176* (2013.01); *G06F 21/32* (2013.01);
(Continued)

(58) Field of Classification Search
CPC .......... G06K 9/00604; G06K 9/00248; G06K 9/00281; G06K 9/00919; G06K 9/0061;
(Continued)

(56) References Cited

U.S. PATENT DOCUMENTS

| 8,705,808 B2 | 4/2014 | Determan et al. |
| 8,797,140 B2 | 8/2014 | Shinzaki |

(Continued)

FOREIGN PATENT DOCUMENTS

| JP | 2005-242677 A | 9/2005 | |
| JP | 2005242677 | * 9/2005 | ............... G06F 1/00 |

(Continued)

OTHER PUBLICATIONS

Omid Sharifi et al, "Optimal Face-Iris, Multimodal Fusion Scheme", Symmetry, vol. 8, No. 6, Jun. 15, 2016, p. 48, XP055501494.
(Continued)

*Primary Examiner* — Leon Viet Q Nguyen
(74) *Attorney, Agent, or Firm* — Jefferson IP Law, LLP

(57) ABSTRACT

An iris-based authentication method is provided. The method includes emitting light of an infrared wavelength band and obtaining an image based on the light of the infrared wavelength band, determining whether a specified condition is satisfied, if the specified condition is satisfied, performing user authentication (e.g., complex authentication) based on at least part of a face image and an iris image of the image that a biometric sensor obtains, or, if the specified condition is not satisfied, performing the user authentication (e.g., iris-only authentication) based on the iris image in the image that the biometric sensor obtains.

19 Claims, 15 Drawing Sheets

(51) Int. Cl.
*G06F 21/32* (2013.01)
*G06K 9/20* (2006.01)

(52) U.S. Cl.
CPC ..... *G06K 9/00597* (2013.01); *G06K 9/00617* (2013.01); *G06K 9/00892* (2013.01); *G06K 9/2018* (2013.01); *G06K 9/2027* (2013.01)

(58) Field of Classification Search
CPC ...... G06K 9/036; G06K 9/00912; G06K 9/00; H04N 5/23219
See application file for complete search history.

(56) References Cited

U.S. PATENT DOCUMENTS

| | | | | |
|---|---|---|---|---|
| 2006/0139447 | A1* | 6/2006 | Unkrich | H04N 13/31 348/51 |
| 2008/0075334 | A1* | 3/2008 | Determan | G06K 9/00255 382/117 |
| 2008/0211627 | A1 | 9/2008 | Shinzaki | |
| 2016/0253559 | A1* | 9/2016 | Goncharov | G06K 9/00288 348/78 |
| 2016/0335495 | A1* | 11/2016 | Kim | G06K 9/00248 |
| 2016/0364561 | A1 | 12/2016 | Lee | |
| 2017/0109511 | A1* | 4/2017 | Dass | H04N 5/2351 |

FOREIGN PATENT DOCUMENTS

| | | |
|---|---|---|
| JP | 2008-217355 A | 9/2008 |
| JP | 2010-079609 A | 4/2010 |
| KR | 10-2004-0076962 A | 9/2004 |
| KR | 10-2016-0012636 A | 2/2016 |

OTHER PUBLICATIONS

Bharadwaj S et al, "Periocular Biometrics: When iris recognition fails", Biometrics: Theory Applications Andsystems (BTAS), 2010 Fourth IEEE International Conference on, IEEE, Piscataway, NJ, USA, Sep. 27, 2010, pp. 1-6, XP031800522.
European Search Report dated Aug. 30, 2018, issued in European Patent Application No. 18164188.7.

* cited by examiner

METHOD OF RECOGNITION BASED ON IRIS RECOGNITION AND ELECTRONIC DEVICE SUPPORTING THE SAME

CROSS-REFERENCE TO RELATED APPLICATION(S)

This application is based on and claims priority under 35 U.S.C. § 119 to Korean Patent Application No. 10-2017-0038207, filed on Mar. 27, 2017, in the Korean Intellectual Property Office, the disclosure of which is incorporated by reference herein in its entirety.

TECHNICAL FIELD

The disclosure relates to an iris-based authentication function.

BACKGROUND

Nowadays, various types of portable electronic devices such as a smartphone, a tablet personal computer (PC), and the like have been widely distributed. The portable electronic devices support the iris authentication function with regard to a security function.

The above information is presented as background information only to assist with an understanding of the present disclosure. No determination has been made, and no assertion is made, as to whether any of the above might be applicable as prior art with regard to the disclosure.

SUMMARY

Aspects of the disclosure are to address at least the above-mentioned problems and/or disadvantages and to provide at least the advantages described below. Accordingly, an aspect of the disclosure is to provide an electronic device that activates an infra-red (IR) camera device to obtain a user's iris image and may determine whether the obtained iris image is the same as the stored information. The iris authentication function analyzes an image obtained by using the IR camera device to guide the user's iris to be placed at a predefined specific point at a specific size. In this case, it is difficult to detect an iris area by using an IR camera device, the capture angle of which is relatively narrow, and it may take a long time to analyze the image, since there is a need for a relatively large load to detect the iris area based on the obtained IR image. Accordingly, the accuracy may also be relatively low.

Another aspect of the disclosure is to provide an iris-based authentication method capable of saving power or improving an iris recognition speed, and an electronic device supporting the same.

Another aspect of the disclosure is to provide an iris-based authentication method that is capable of reducing a false rejection rate (FRR) in the image-based authentication manner, and an electronic device supporting the same.

In accordance with an aspect of the disclosure, an electronic device is provided. The electronic device includes a biometric sensor including a light emitting element emitting light of an infrared wavelength band and an infrared camera obtaining an image based on the light of the infrared wavelength band, a memory storing data, which is compared with the image obtained based on the biometric sensor, and a processor operatively connected to the biometric sensor and the memory. The processor is configured to determine whether a specified condition is satisfied, if the specified condition is satisfied, to perform user authentication based on at least part of a face image and an iris image of the image that the biometric sensor obtains, and if the specified condition is not satisfied, to perform the user authentication based on the iris image in the image that the biometric sensor obtains.

In accordance with another aspect of the disclosure, an iris-based authentication method is provided. The method includes emitting light of an infrared wavelength band and obtaining an image based on the light of the infrared wavelength band, determining whether a specified condition is satisfied, if the specified condition is satisfied, performing user authentication (e.g., complex authentication) based on at least part of a face image and an iris image of the image that a biometric sensor obtains, or, if the specified condition is not satisfied, performing the user authentication (e.g., iris-only authentication) based on the iris image in the image that the biometric sensor obtains.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figure 1:
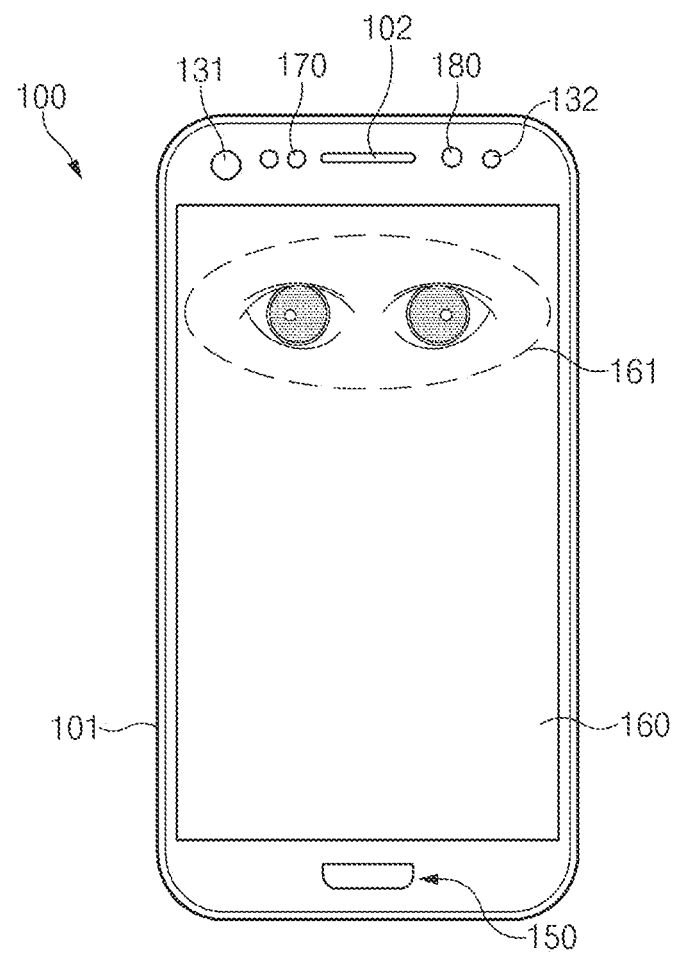
FIG. 1 is a view illustrating an example of an external appearance of an electronic device including a biometric sensor according to an embodiment of the disclosure.

The following description with reference to the accompanying drawings is provided to assist in a comprehensive understanding of various embodiments of the present disclosure as defined by the claims and their equivalents. It includes various specific details to assist in that understanding, but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the disclosure. Accordingly, it should be apparent to those skilled in the art that the following description of various embodiments of the present disclosure is provided for illustration purposes only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

According to various embodiments disclosed in the disclosure, the electronic device may include various types of devices. For example, the electronic device may include at least one of a portable communication device (e.g., a smartphone), a computer device (e.g., a personal digital assistant (PDA), a tablet personal computers (PCs), a laptop PC, a desktop PC, a workstation, or a server), a portable multimedia device (e.g., an e-book reader or a Motion Picture Experts Group phase 1 or phase 2 (MPEG-1 or MPEG-2) audio layer 3 (MP3) player), a portable medical device (e.g., a heart rate, blood glucose, blood pressure, or a thermometer), a camera, or a wearable device. A wearable device may include at least one of an accessory type of a device (e.g., a timepiece, a ring, a bracelet, an anklet, a necklace, glasses, a contact lens, or a head-mounted device (HMD)), one-piece fabric or clothes type of a device (e.g., electronic clothes), a body-attached type of a device (e.g., a skin pad or a tattoo), or a bio-implantable circuit. The electronic device may include at least one of, for example, televisions (TVs), digital versatile disc (DVD) players, audio devices, audio accessory devices (e.g., a speaker, a headphone, or a headset), a refrigerator, an air conditioner, a cleaner, an oven, a microwave oven, a washing machine, an air cleaner, a set-top box, a home automation control panel, a security control panel, a game console, an electronic dictionary, an electronic key, a camcorder, or an electronic picture frame.

The electronic device may include at least one of a navigation device, a global navigation satellite system (GNSS), an event data recorder (EDR) (e.g., a black box for a car, a ship, or a plane), a vehicle infotainment device (e.g., a head-up display for a vehicle), an industrial or home robot, a drone, an automated teller machine (ATM), a point of sales (POS) device, a measurement device (e.g., a water meter, an electricity meter, or a gas meter), or Internet of things (e.g., a light bulb, a sprinkler device, a fire alarm, a thermostat, or a street lamp). The electronic device is not limited to the above-described devices. For example, similarly to a smartphone having function of measuring personal bio-information (e.g., a heart rate or blood glucose), the electronic device may provide functions of multiple devices in the complex manner. In the present disclosure, the term "user" used herein may refer to a person who uses the electronic device or may refer to a device (e.g., an artificial intelligence electronic device) that uses the electronic device.

FIG. 1 is a view illustrating an example of an external appearance of an electronic device including a biometric sensor according to an embodiment of the disclosure.

Referring to FIG. 1, an electronic device 100 according to an embodiment of the disclosure may include a housing 101, device elements (e.g., a display 160, a biometric sensor (e.g., an iris sensor 131 or 132), an input interface 150, and a sensor 170) seated inside the housing 101. Additionally or alternatively, the electronic device 100 may further include a receiver 102 and a red, green blue (RGB) camera 180. The electronic device 100 may further include a printed circuit board seated inside the housing 101, and a processor, which controls the driving of the display 160 and the iris sensor 131 or 132, the input interface 150, the sensor 170, or the like, a memory, and the like may be mounted in the printed circuit board.

The housing 101 may include a first surface, a second surface opposite to the first surface, and at least one side area interposed between the first surface and the second surface. The first surface may be opened, and at least part of the display 160 may be exposed to the outside through the first surface. The upper portion of the side area of the housing 101 may surround an external appearance of the seated display 160, and a hole associated with the input interface 150 may be provided on at least one side of the side area. A protective cover (e.g., cover glass) disposed on the uppermost layer of the display 160 may be included in a configuration of the housing 101. The periphery of the display 160 may be formed as a curved portion having a specified curvature. In the case where the periphery of the display 160 is formed as a curved portion, the periphery of the display 160 may be disposed in at least part of the side area of the housing 101. A printed circuit board on which a processor and a memory associated with the driving the display 160 are mounted may be disposed inside the housing 101.

The RGB camera 180 may be disposed on the first surface of the housing 101. The RGB camera 180 may capture an image based on light generated from an external light source (e.g., light of the sun, an indoor light source, or the like). The RGB camera 180 may be disposed on the front surface of the housing 101 (e.g., the first surface on which the display 160 is disposed) so as to be used to obtain a selfie (a self-camera image). According to various embodiments, the electronic device 100 may further include an RGB camera exposed in the back direction of the housing 101.

The display 160 may be disposed on at least part of the first surface of the housing 101. The display 160 may include a display area and a non-display area. For example, the display 160 may output a specified object 161 or a screen associated with iris authentication or complex authentication. The specified object 161 may include an image for guiding a relative location between the electronic device 100 and the user's eyes associated with the iris authentication. Alternatively, the specified object 161 may include an image for guiding (or indicating) a relative location between the electronic device 100 and the user's face and eyes associated with the complex authentication. To cope with the issue, the user may move the electronic device 100 or may move his/her face to align the user's eyes (e.g., an image of the user's eye obtained through the iris sensor 131 or 132) output to the display 160 with a specified guide image (e.g., an image of an ellipse set to align the user's eye). In this operation, the display 160 may output information (e.g., at least one of an image or a text) associated with the progress of the iris authentication or the complex authentication. For example, the display 160 may output at least one of guide information for guiding a user's eyes or face to move in a specified direction, how much the user's eyes or face is aligned with the guide image, the obtainment of an image according to the alignment of the user's eyes or face with the guide image, information about whether the iris authentication or the complex authentication is performed, or information about whether the iris authentication or the complex authentication is successful.

The input interface 150 may include at least one device configuration capable of generating a user input. For example, the input interface 150 may include a home key disposed on the first surface of the housing 101, at least one button key disposed in the side area of the housing 101, or the like. The input interface 150 may further include a microphone capable of collecting a user voice. For example, the input interface 150 may receive a user input associated with an operation of the iris sensor 131 or 132. In the case where the display 160 is provided in the form of a touch screen, the display 160 may be included in the input interface 150. The display 160 may further include a digitizer, or the like, and the display 160 may collect a user input according to the operation of a stylus pen, or the like.

Additionally or alternatively, the electronic device 100 may further include the receiver 102, a speaker, or the like that is associated with an audio output. The receiver 102 may be disposed on the first surface of the housing 101. For example, the speaker may be disposed on the side area of the housing 101 or the second surface (or the first surface) of the housing 101.

The sensor 170 may be disposed on one side (e.g., the first surface of the housing 101) of the electronic device 100. For example, the sensor 170 may include at least one of an illuminance sensor sensing external illuminance, a proximity sensor determining whether an object is approaching, a time-of-flight (TOF) sensor sensing a distance between an object and the electronic device 100, a touch sensor determining whether an object is contacted, or a pressure sensor sensing how much an object is pressed. The electronic device 100 may perform one of iris authentication or complex authentication depending on illuminance information that the illuminance sensor in the sensor 170 collects. Alternatively, the electronic device 100 may perform one of iris authentication or complex authentication depending on an access degree of the object obtained by the proximity sensor.

The iris sensor 131 or 132 may include the light emitting unit 131 emitting light of a specified wavelength band (e.g., an infrared wavelength band) and an infrared camera (e.g., the iris camera 132) obtaining an image (e.g., an IR image) corresponding to the light of the specified wavelength band. The light emitting unit 131 may emit the light of the specified wavelength band. For example, the light emitting unit 131 may include at least one of an infrared light emitting diode (IR-LED) or an IR-LD. The iris camera 132 may obtain a subject image under control of a processor. The iris camera 132 may transmit the obtained subject image to the processor. The electronic device 100 may include a processor for iris sensing (or an integrated circuit (IC) for iris sensing) associated with iris recognition, and the processor for iris sensing may control the operation of the iris sensor 131 or 132. The processor for iris sensing may compare an iris image pre-stored in a memory or pieces of minutiae information corresponding to the iris image with the currently obtained iris image or minutiae information extracted from the currently obtained iris image. For example, the minutiae information may include iris information extracted from at least one iris image, for example, an iris template. The iris template may include digital data corresponding to information extracted from the iris image. With regard to the iris authentication, in the case of registering a plurality of iris images, a plurality of iris templates may be stored. The plurality of iris templates may be used to compare with the obtained iris image, and whether an iris authentication is successful may be determined depending on a difference between an iris image and each of the iris templates.

A processor (or a processor for iris sensing; the description below is based on a processor) seated inside the housing 101 may perform iris-only authentication or complex authentication depending on whether a specified condition is satisfied. For example, in the case where an external illuminance environment is not less than a specified illuminance value, the electronic device 100 may perform the complex authentication. In the case where a distance between the user's face and the iris camera 132 is not less than a specified distance (or in the case where the user's face is spaced apart from the iris camera 132 by a specified distance or more), the electronic device 100 may perform the complex authentication. In the case where a distance between the user's face (or a subject) and the iris camera 132 is not less than a specified distance (e.g., a long distance environment) while an illuminance value corresponding to an outdoor environment is detected, the electronic device 100 may perform the complex authentication. The outdoor environment may be determined as a specified illumination range value capable of being distinguished from the illumination range values of an indoor environment, and the illuminance range for distinguishing an indoor environment from an outdoor environment may be changed depending on settings. The long distance environment may be determined as the specified distance value capable of being distinguished from the distance values of a short distance environment, and the distance magnitude for distinguishing the long distance from the short distance may be changed depending on settings.

As described above, in the case where at least one of the external illuminance value or a distance between the iris camera 132 and a subject satisfies a specified condition, the electronic device 100 may perform the complex authentication.

With regard to performing the complex authentication, the electronic device 100 may simultaneously or sequentially operate a process of comparing at least part of the user's face with the pre-stored face information, for example, a face template (e.g., the pre-stored face information of the user, minutiae information of the user's face, or information obtained by converting the minutiae of the face into digital data) and a comparison process of an iris image. Even though the comparison value (hereinafter, referred to as an "iris difference value"; it is determined that the currently obtained iris image is valid, if the iris difference value is less than the first threshold value) between the currently obtained iris image and an iris template is not less than a first threshold value (e.g., in the case where an iris difference value between the obtained iris image and the preset iris templates is not less than a specified value), in the case where the comparison result (hereinafter, referred to as a "face difference value"; as the face difference value is relatively low, it is determined that the degree of coincidence between the currently obtained face image and the specified face template is high or it is determined that the currently obtained face image is valid) between the currently obtained face image and the face template is not greater than a specified value (e.g., in the case where the face difference value between at least part of the obtained face image and the pre-stored face template is not greater than the specified value), the electronic device 100 may determine that the authentication is successful.

As described above, the electronic device 100 according to an embodiment of the disclosure may maintain security performance of a degree of satisfaction or more while reducing the failure probability or a FRR in the iris authentication, by adding face authentication in addition to the iris authentication depending on a condition.

Figure 2:
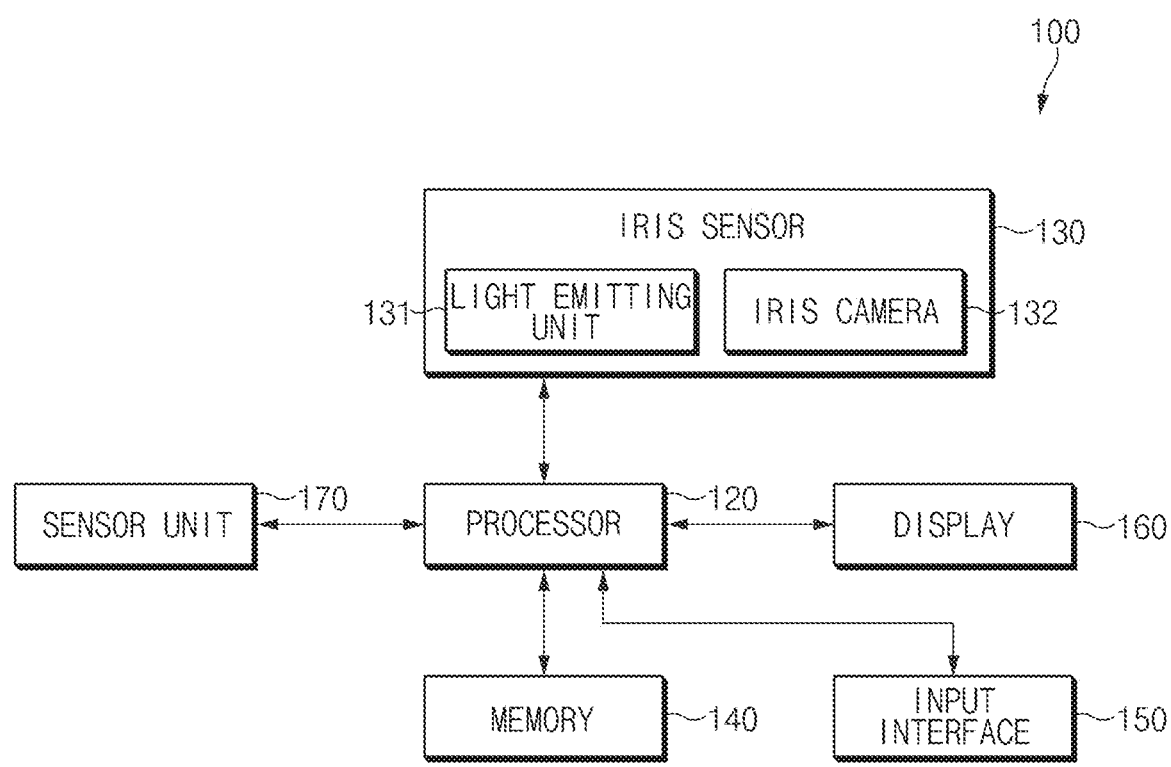
FIG. 2 is a block diagram illustrating an example of a configuration of an electronic device according to an embodiment of the disclosure.

FIG. 2 is a block diagram illustrating an example of a configuration of an electronic device according to an embodiment of the disclosure.

Referring to FIGS. 1 and 2, the electronic device 100 may further include a processor 120, a memory 140, an iris sensor 130, the input interface 150, the display 160, the sensor unit 170, and the like. Additionally, the electronic device 100 may further include a housing in which the elements are seated, and may further include an RGB camera, at least one communication circuit supporting a communication function, an antenna connected to the communication circuit, or the like.

As described above in FIG. 1, the input interface 150 may include at least one means or at least one user interface (UI), which is capable of generating an input signal corresponding to a user input. The input interface 150 may include a physical button associated with the execution of an iris authentication function. The input interface 150 may include a touch key or a touch screen display panel, which is associated with the execution of the iris authentication function. In this case, the input interface 150 may include the display 160 in which an icon associated with the execution of the iris authentication function is displayed.

The memory 140 may store at least one application program associated with the operation of the electronic device 100. The memory 140 may include an authentication program associated with the operation of the iris sensor 130. For example, the authentication program may include an instruction set that checks a specified condition to determine whether to perform iris-only authentication or whether to perform complex authentication (e.g., perform face authentication and iris authentication at the same time and determine whether authentication is successful, depending on the processed result), an instruction set that performs iris-only authentication depending on the checking of a specified condition and then outputs the result, an instruction set that performs complex authentication depending on a specified condition and then outputs the result. In this regard, the memory 140 may store at least one iris information, for example, an iris template (e.g., reference data for iris authentication generated based on an iris image registered in association with iris authentication, as the pre-stored information) and at least one face template (e.g., reference data for face authentication generated based on at least part of a face image registered in association with at least part of face authentication, as the pre-stored information). The memory 140 may store at least one face template for each face portion. For example, the memory 140 may store at least one face template associated with the entire face (e.g., a face above neck), at least one face template associated with the eyeball area (e.g., two eyes and the peripheries of the eyes, a part of the face including the middle of the forehead), at least one face template associated with a first eye (e.g., the left eye and the periphery of the left eye), and at least one face template associated with a second eye (e.g., the right eye and the periphery of the right eye).

The iris sensor 130 may include the light emitting unit 131 and the iris camera 132. Additionally or alternatively, the iris sensor 130 may further include an iris sensing controller (or a processor for iris sensing) that controls the operations of the light emitting unit 131 and the iris camera 132. The processor for iris sensing may be included in the processor 120 or may be disposed in the iris sensor 130.

The light emitting unit 131 may emit the light of a specified wavelength band under control of one of the processor for iris sensing or the processor 120. For example, the light emitting unit 131 may output the light of an infrared wavelength band at a specified time point (e.g., at a point in time when iris sensing is requested). Depending on the control, the light emitting unit 131 may emit the light of the infrared wavelength during a specified period and may be turned off automatically if the specified period ends. The light emitting unit 131 may vary the intensity of light to be emitted, depending on the control. For example, the light emitting unit 131 may output infrared light of a specified first intensity depending on a specified first condition (e.g., in the case where an external illuminance value is not less than a specified value, in the case where a face is spaced apart from the iris camera 132 by a specified distance or more, or the like). The light emitting unit 131 may output the infrared light, the intensity of which is a specified second intensity (e.g., the intensity relatively lower than the first intensity), depending on a specified second condition (e.g., in the case where an external illuminance value is not greater than a specified value, in the case where a face is spaced apart from the iris camera 132 by less than a specified distance, or the like). The light emitting unit 131 may emit the infrared light of a specified intensity regardless of a condition, depending on the control.

The iris camera 132 may obtain an IR image associated with an iris or a face, based on the light emitted by the light emitting unit 131 and may transmit the obtained IR image to the processor for iris sensing or the processor 120. In this operation, the iris camera 132 may obtain an IR preview image (e.g., the preview image obtained based on an infrared wavelength) associated with, for example, the iris-related eye area of a user, under control of the processor for iris sensing. Under control of the processor for iris sensing, the iris camera 132 may determine whether the iris area is obtained above a specified size from the IR preview image and may automatically obtain an IR still image associated with an iris if the iris area is obtained above the specified size. The iris camera 132 may obtain IR still images at a specified period or in response to a user input, without obtaining the IR preview image.

The processor for iris sensing may control the emission time point of the light emitting unit 131 and may control the iris camera 132 to obtain the IR image (e.g., an IR preview image or at least one IR still image). The processor for iris sensing may receive a request associated with an iris operation from the processor 120 if an iris recognition-related application is executed, and may activate the light emitting unit 131 depending on the operation of a received iris authentication function. The processor for iris sensing may obtain the image of a subject by using the iris camera 132. In this operation, the processor for iris sensing may determine whether an iris-only authentication condition or a complex authentication condition is satisfied. Depending on the satisfied condition, the processor for iris sensing may perform one authentication of the iris-only authentication or the complex authentication.

The display 160 may output at least one screen associated with the operation of the electronic device 100. For example, the display 160 may output a lock screen or the like in response to a user input. Alternatively, the display 160 may output a screen for requesting the execution of an application, the security of which is set. To unlock a screen, the security of which is set, or to execute a function, the security of which is set, the display 160 may output a screen associated with the processing of the iris authentication function. For example, the display 160 may output at least part of a preview image and a specified UI (e.g., guide information for adjusting the face location of a user in association with iris recognition) in association with the processing of the iris authentication function. The display 160 may output an IR image (e.g., an IR preview image or an IR still image) that the iris camera 132 obtains. The IR image may include an iris image and an image association with the periphery of an iris (e.g., an eyeball area, the periphery of the eyes, a part of a nose, a cheek or a lip, eyebrow, or the like) of the user. The display 160 may output a message associated with iris recognition failure or iris recognition success. When the iris authentication function or the complex authentication function is successful, the display 160 may output an execution of screen of a specified function under control of the processor 120.

The display 160 may output the guide information for guiding whether to perform iris-only authentication or whether to perform complex authentication, depending on the satisfied condition. Upon performing the iris-only authentication, the display 160 may display a guide object to be aligned with the eyes of the user. Upon performing the complex authentication, the display 160 may display the guide object corresponding to a portion (e.g., at least part of a face and an iris) to be aligned, depending on the satisfied condition. The display 160 may output an image or a text (e.g., a number, a graph, or a bar corresponding to the numerical value, or the like) corresponding to the degree of alignment (e.g., the degree of alignment between the eye alignment guide object and the captured iris image or the iris image in preview image, or the degree of alignment between the guide object corresponding to the face area and the face image). The display 160 may output a guide object having a different part of a face on which the complex authentication is performed, depending on the satisfied condition. For example, the display 160 may output a guide object for aligning the entire face, the periphery of two eyes, or the periphery of one eye, depending on the intensity of an external illuminance.

According to various embodiments of the present disclosure, the processor 120 may transmit and process a signal associated with the function control of the electronic device 100. In response to an execution request of an iris-based authentication function, the processor 120 may determine whether a specified condition is satisfied, determine whether to perform the iris-only authentication or whether to perform the complex authentication, and may perform the authentication function according to the determination. In this operation, the processor 120 may replace the processor for iris sensing or may control the operation of the processor for iris sensing. For example, in the case where the processor 120 has a structure in which there is no processor for iris sensing, the processor 120 may control the light emitting time point of an infrared wavelength, the obtainment of an infrared-based iris image and the periphery image of eyes, an authentication function execution based on the comparison of the obtained image, or the like by directly controlling the light emitting unit 131 and the iris camera 132.

Figure 3:
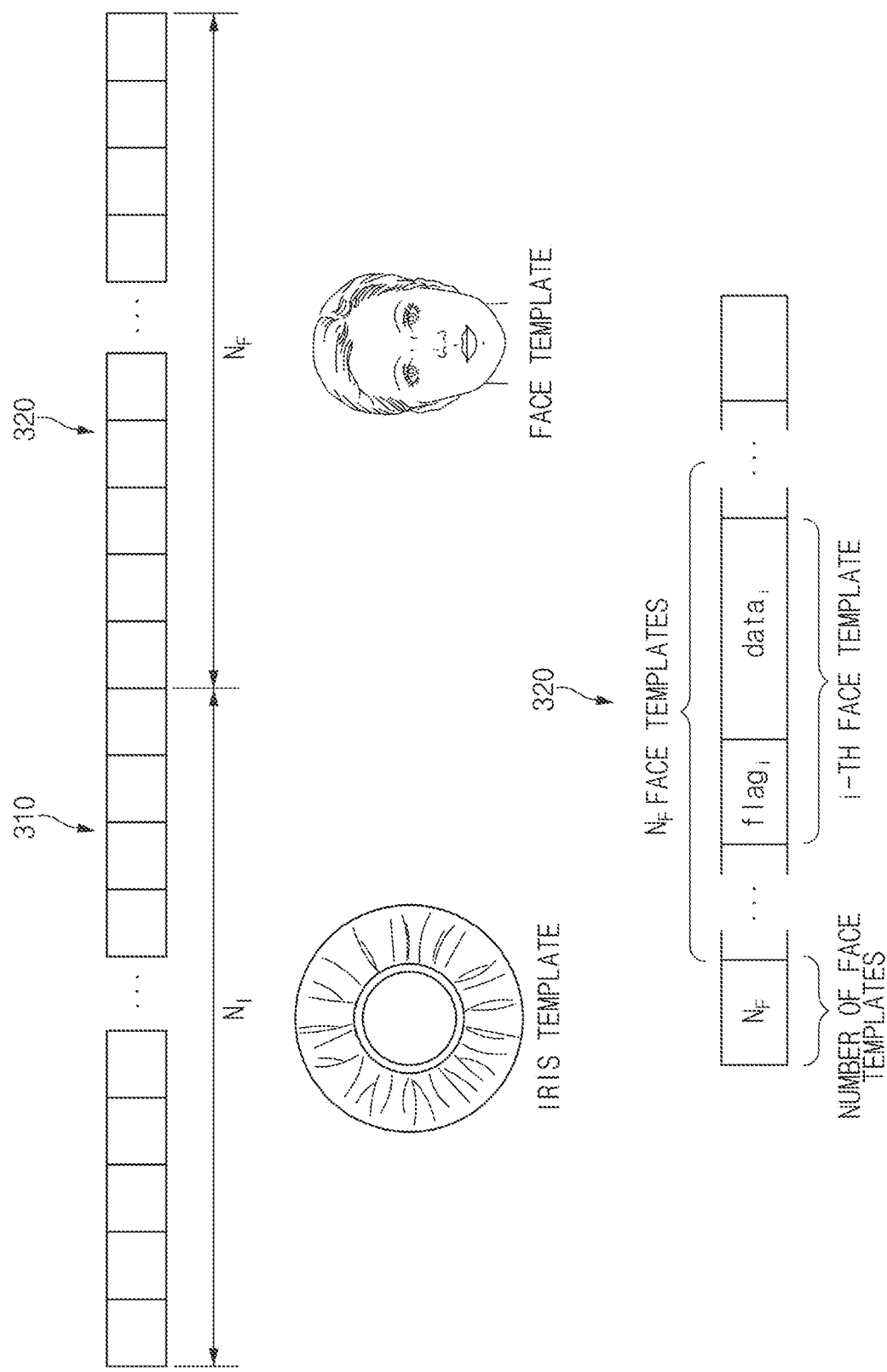
FIG. 3 is a view of an example of a template structure according to an embodiment of the disclosure.

FIG. 3 is a view for describing an example of a template structure according to an embodiment of the disclosure.

Referring to FIG. 3, the memory 140 of the electronic device 100 according to an embodiment of the present disclosure may store an iris template 310 and a face template 320. For example, the iris template 310 may be stored, for example, as many as $N_I$. In this regard, the user may capture a plurality of iris images and may register the iris template 310 associated with each of the captured plurality of iris images. The processor 120 may extract the iris template 310 from each of the plurality of iris images. With regard to the extraction of the iris template 310, the processor 120 may perform filtering or the like to detect minutiae from an iris image and may generate a digital code for the arrangement state of the detected minutiae. The processor 120 may store the generated digital code as the iris template 310. For example, the memory 140 storing the iris template 310 may include bits recording information about the number of plurality of iris templates 310, bits recording the order of the iris templates 310, and bits storing a digital code value corresponding to the iris template 310.

For example, the face template 320 may be stored, for example, as many as $N_F$. The memory 140 may store the face templates 320 extracted based on a plurality of face images. In this regard, as illustrated in FIG. 3, the memory 140 may include bits designating the number of face templates 320, bits designating the order of face templates 320, and bits storing a digital code corresponding to the face template 320. For example, the memory 140 may store the entire face templates 320 extracted based on a plurality of entire face images. Alternatively, the memory 140 may store the partial face templates 320 extracted based on at least partial face images. The memory 140 may store at least one entire face template, a first partial face template associated with at least one first face portion (e.g., a left eye and the periphery of the left eye), a second partial face template associated with at least one second face portion (e.g., a right eye and the periphery of the right eye), or the like.

An embodiment is above exemplified as the plurality of iris templates 310 and the plurality of face templates 320 are stored. However, embodiments of the disclosure may not be limited thereto. For example, the at least one iris template 310 and the at least one face template 320 may be stored in the memory 140. The number of iris templates 310 may be the same as the number of face templates 320, and the iris templates 310 and the face templates 320 may be stored in the memory 140. The specific iris template 310 may be linked with the specified face template 320 and may be operated. As such, upon performing complex authentication, the specified iris template 310 and the specified face template 320 may be used to compare the currently obtained iris image and at least part of face image.

Figure 4:
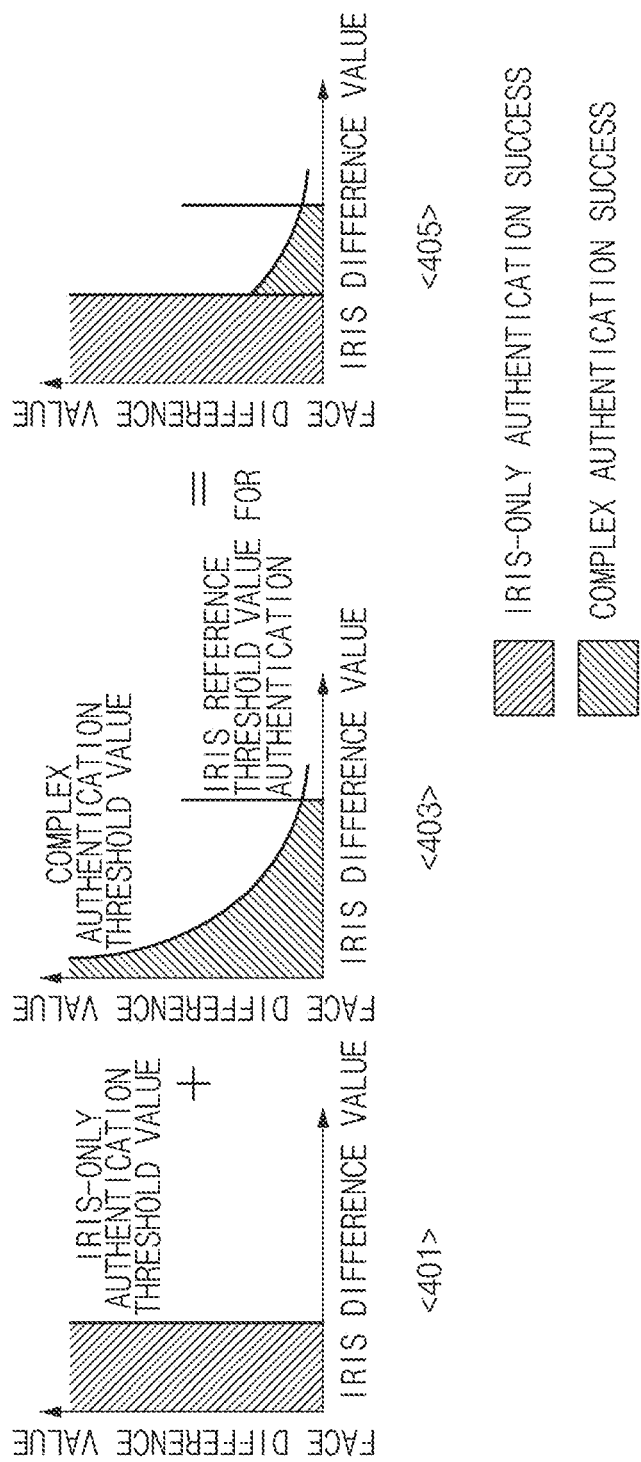
FIG. 4 is a view of an example of authentication success probability expansion according to an embodiment of the disclosure.

FIG. 4 is a view for describing an example of authentication success probability expansion according to an embodiment of the disclosure.

Referring to FIG. 4, with regard to authentication success reference, in the case of performing iris-only authentication in a graph in which abscissa denotes an iris difference value (e.g., as a difference value between the pre-stored iris template 310 and the currently obtained iris template, that is, an iris difference value decreases, a matching rate between an iris image and an iris template increases) and ordinate denotes a face difference value (e.g., as a difference value between the pre-stored face template 320 and the currently obtained face template, that is, a face difference value decreases, the matching rate increases), as illustrated in state 401, the authentication success rate associated with the iris-only authentication may be determined by a first threshold value associated with an iris difference value. The first threshold value may be a reference value for determining whether to perform iris-only authentication that is based on the iris difference value between the pre-stored iris template 310 and the currently obtained iris template or whether to perform complex authentication that is based on the face image and the iris image. The first threshold value may be determined at the time of security performance settings and may be adjusted depending on the change of user settings. In the case where the iris difference value is less than the first threshold value (e.g., in the case where the difference value between the pre-stored iris template 310 and the currently obtained iris template is less than the first threshold value), the processor 120 may determine that the currently obtained iris template is similar to the pre-stored iris template 310 by a reference value or more and may determine that iris authentication is successful.

With regard to the authentication success reference, in the case of performing complex authentication in a graph in which abscissa denotes the iris difference value and ordinate denotes the face difference value, as illustrated in state 403, the authentication success rate associated with the complex authentication may be defined. With regard to the authentication success reference associated with the iris-only authentication or the complex authentication, if the iris-based authentication is requested, the processor 120 may obtain an iris image, and, as described above in state 401, may compare with the pre-stored iris template to determine authentication success according to the iris-only authentication in the case where the iris difference value is less than a specified first threshold value. If the iris difference value is greater than the specified first threshold value and is less than a specified second threshold value (a value that is greater than the first threshold value by a specified magnitude), the processor 120 may obtain at least part of face image based on an IR image.

With regard to a face image, the processor 120 may compare with the pre-stored face template to calculate the face difference value. In this operation, even though the face difference value is relatively great, in the case where the iris difference value is relatively small, the processor 120 may determine that the complex authentication is successful. Alternatively, even though the iris difference value is relatively great, in the case where the face difference value is relatively small, the processor 120 may determine that the complex authentication is successful. In the case where the iris difference value is not less than the second threshold value, the processor 120 may not perform the complex authentication. In this operation, the processor 120 may output a message associated with the unavailable authentication function, which is based on the iris sensor 130, or an environment adjustment request message (e.g., a request message for moving to the indoor environment) for obtaining the IR image.

With regard to the authentication success reference, the electronic device 100 may set the authentication success reference based on a graph of state 405 obtained by combining the above-described graph of state 401 and the above-described graph of state 403. For example, in the case where the iris difference value is less than the first threshold value associated with the iris-only authentication, the processor 120 may determine that the authentication is successful, regardless of the face difference value. In the case where the iris difference value is not less than the first threshold value associated with the iris-only authentication (or in the case where the iris difference value is not less than the first threshold value and is less than the second threshold value), the processor 120 may determine whether the authentication is successful, depending on the face difference value. In a state where the iris difference value is not less than the first threshold value associated with the iris-only authentication, in the case where the face difference value is relatively small even though the iris difference value is relatively great, the processor 120 may determine that the complex authentication is successful. In this operation, in the case where the processor 120 applies the iris difference value for the complex authentication and then the iris difference value is greater than a specific reference value (or in the case where a difference between the currently obtained iris image and the pre-stored iris template is greater than a reference value (e.g., the second threshold value or more)), the processor 120 may determine that the complex authentication fails, regardless of the face difference value.

Figure 5:
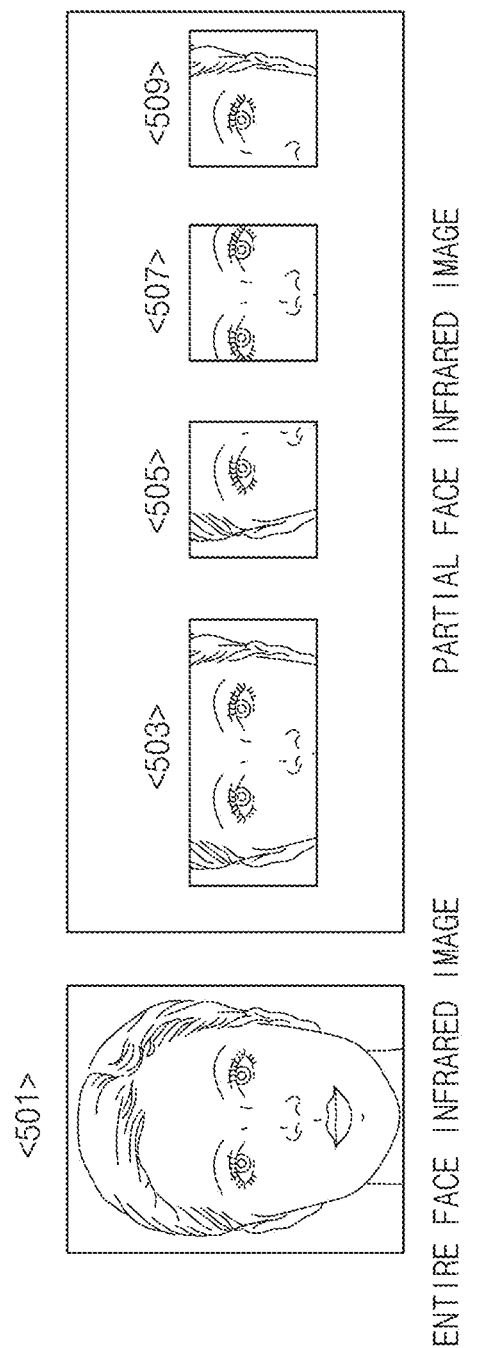
FIG. 5 is a view illustrating an example of a face template according to an embodiment of the disclosure.

FIG. 5 is a view illustrating an example of a face template according to an embodiment of the disclosure.

Referring to FIG. 5, with regard to a face template applied to an iris-based authentication function according to an embodiment of the disclosure, as illustrated in state 501, the processor 120 may obtain the entire face image obtained based on infrared light. The entire face template corresponding to the entire face may include a digital code corresponding to minutiae associated with a line, a forehead, two eyes, a nose, a mouth, a jaw, the middle of the forehead, or ears of the face.

As illustrated in state 503, the processor 120 may obtain a first partial face image including two eyes, the forehead, and the periphery of two eyes, which are obtained based on the infrared light. The first partial face template corresponding to the first partial face image may include a digital code corresponding to minutiae associated with the two eyes, the middle of the forehead, a nose, ears, a part of a face line at the periphery of ears, and the like.

As illustrated in state 505, the processor 120 may include a second partial face image including the right eye and the periphery of the right eye, which are obtained based on the infrared light. The second partial face template corresponding to the second partial face image may include a digital code corresponding to minutiae associated with the right eye, a part of a nose, a part of the middle of the forehead, a part of a cheek, the right ear, and the like.

As illustrated in state 507, the processor 120 may include a third partial face image including two eyes and the periphery of the two eyes, which are obtained based on the infrared light. The third partial face template corresponding to the third partial face image may include a digital code corresponding to minutiae associated with the two eyes, a nose, the middle of the forehead, and the like.

As illustrated in state 509, the processor 120 may obtain a fourth partial face image including the left eye and the periphery of the left eye, which are obtained based on the infrared light. The fourth partial face template corresponding to the fourth partial face image may include a digital code corresponding to minutiae associated with the left eye, a part of a nose, a part of the middle of the forehead, a part of a cheek, the left ear, and the like.

With regard to the operation of above-described various face templates, a user may perform infrared capture and registration on the entire face or various portions of the face. Alternatively, the processor 120 may obtain the above-described partial face images from the entire face image of the user obtained based on the infrared capture and may extract partial face templates based on the obtained partial face images.

An electronic device according to an embodiment of the disclosure may include a biometric sensor (e.g., iris sensor) including a light emitting unit emitting light of an infrared wavelength band and an infrared camera obtaining an image based on the light of the infrared wavelength band, a memory configured to store data, which is compared with images obtained based on the biometric sensor, and a processor operatively connected to the biometric sensor and the memory. The processor may be configured to obtain an iris difference value by comparing iris image information (e.g., currently obtained iris image-based iris template) with the pre-stored iris image information (e.g., pre-stored iris template) and to perform user authentication (e.g., complex authentication) based on at least part of a face image and the iris image the image that the biometric sensor obtains, in the case where the obtained iris difference value is not less than a first threshold value (or is not less than the first threshold value and is less than a second threshold value). The processor may determine whether an iris difference value exceeds the first threshold value, may perform complex authentication if the iris difference value exceeds the first threshold value, and may perform complex authentication in the case where the iris difference value is not less than the first threshold value and is less than a second threshold value. Herein, in the case where the iris difference value is not less than the second threshold value, the processor may determine that the authentication fails, without performing complex authentication.

An electronic device according to an embodiment of the disclosure may include a biometric sensor (e.g., an iris sensor) including a light emitting unit emitting light of an infrared wavelength band and an infrared camera obtaining an image based on the light of the infrared wavelength band, a memory storing data, which is compared with images obtained based on the biometric sensor, and a processor operatively connected to the biometric sensor and the memory. The processor may be configured to determine whether a specified condition is satisfied, if the specified condition is satisfied, to perform user authentication (e.g., complex authentication) based on at least part of a face image and an iris image of an image that the biometric sensor obtains, and, if the specified condition is not satisfied, perform the user authentication (e.g., iris-only authentication) based on the iris image in the image that the biometric sensor obtains.

The processor may be configured to execute a first function if user authentication based on an iris image is successful, and to execute a second function different from the first function if user authentication based on the at least part of the face image and the iris image is successful.

The second function may include a function according to the execution of an application, the security level of which is lower than the security level of the first function. In the case where the level of complex authentication is set to be higher (or the level of complex authentication is set to be higher depending on user settings), the second function may include a function according to the execution of an application, the security level of which is higher than the security level of the first function.

The second function may include an access function of the memory area in which the access of the first function is restricted.

An electronic device according to an embodiment of the disclosure may include a biometric sensor (e.g., an iris sensor) including a light emitting unit emitting light of an infrared wavelength band and an infrared camera obtaining an image based on the light of the infrared wavelength band, a memory storing data, which is compared with images obtained based on the biometric sensor, and a processor operatively connected to the biometric sensor and the memory. The processor may be configured to determine whether a specified condition is satisfied, if the specified condition is satisfied, to perform user authentication based on at least part of a face image and an iris image of an image that the biometric sensor obtains, and, if the specified condition is not satisfied, perform the user authentication based on the iris image in the image that the biometric sensor obtains.

The processor may be configured to obtain an illuminance value in association with the specified condition and, if an environment in which the image is obtained is determined as an indoor environment (or is in an indoor environment) based on the obtained illuminance value, to perform the user authentication based on the iris image.

The processor may be configured to obtain an illuminance value in association with the specified condition and, if an environment in which the image is obtained is determined as an indoor environment (or is in an indoor environment) based on the obtained illuminance value and is a long distance environment in which a capture distance between a subject and the biometric sensor is not less than a specified distance, to perform the user authentication based on the at least part of the face image and the iris image.

The processor may be configured to obtain an illuminance value in association with the specified condition and, if it is determined, based on the obtained illuminance value, that an environment in which the image is obtained is an outdoor environment, to perform the user authentication based on the at least part of the face image and the iris image.

The processor may be configured to obtain an illuminance value in association with the specified condition and, if an environment in which the image is obtained is determined as an outdoor environment (or is in an outdoor environment) based on the obtained illuminance value and is a short distance environment in which a capture distance between a subject and the biometric sensor is less than a specified distance, to perform the user authentication based on the at least part of the face image and the iris image.

The processor may obtain an illuminance value in association with the specified condition, and may output at least one of a message for guiding that user authentication based on the at least part of a face image and the iris image is impossible or a message for requesting a distance change or a location change for changing an illuminance environment, in the case where an environment in which the image is obtained is determined as an outdoor environment (or is in an outdoor environment) based on the obtained illuminance value and is a long distance environment in which a capture distance between a subject and the biometric sensor is not less than a specified distance. The processor may perform complex authentication in an outdoor and a long distance environment.

The processor may be configured, if an environment in which the image is obtained is a long distance environment in which a distance between a subject and the infrared camera is not less than a specified distance in association with the specified condition, to perform the user authentication based on the at least part of the face image and the iris image.

The processor may be configured to determine that the environment in which the image is obtained is the long distance environment based on an iris size in the obtained iris image or a distance between two eyes in the obtained at least part of the face image, in association with the specified condition.

The processor may be configured, if an environment in which the image is obtained is a short distance environment in which a distance between a subject and the infrared camera is less than a specified distance in association with the specified condition, to perform the user authentication based on the iris image.

The processor may be configured to collect reference data (e.g., face template) corresponding to at least part of a face image to be compared, from the memory in association with the at least part of the face image.

The processor may be configured to determine a specified area in the at least part of face image depending on an external environment (e.g., indoor/outdoor environment or a distance environment between a subject and a biometric sensor when an image is captured) and to collect reference data corresponding to the determined face area, from the memory.

The processor may be configured, if the user authentication based on the iris image fails, to perform the user authentication based on the at least part of the face image and the iris image.

An electronic device according to an embodiment of the disclosure may include a biometric sensor and a processor. The processor may be configured to obtain first biometric information corresponding to the partial area of an external object by using the biometric sensor, to perform first authentication associated with the first biometric information at a first level (e.g., in the case where an iris difference value is less than a first threshold value (e.g., in the case where a difference value between the obtained iris image and the preset iris templates is less than a specified first threshold value) a condition that iris authentication is performed) in the case where the first authentication satisfies a first specified condition, to execute a specified function (e.g., the first specified condition is to execute a function associated with authentication success in the case where authentication is successful) in the case where the first authentication satisfies a second specified condition (e.g., the second specified condition is the case where authentication fails), to perform second authentication associated with the external object at a second level (e.g., for example, the execution of the second level authentication may perform authentication for determining that authentication is successful, even though the iris difference value is not less than the first threshold value (e.g., in the case where a difference value between the obtained iris image and the preset iris templates is not less than the specified first threshold value), in the case where a face difference value is not greater than a specified reference value (e.g., the similarity between the obtained at least part of a face image and the pre-stored face template is not less than a specified value) by using second biometric information obtained by using the first biometric information and the biometric sensor, and to execute the specified function based on the second authentication.

The processor may be configured to include iris information corresponding to the iris of the external object as a part of the first biometric information.

The processor may be configured to include face information corresponding to at least part of a face of the external object as a part of the second biometric information.

The electronic device may include a biometric sensor and a processor. The processor may be configured to receive a request for biometric authentication of a user, to verify context information (e.g., ambient context information evaluated based on pieces of sensor information obtained through at least one sensor) associated with the electronic device based on the request, in the case where the context information satisfies a first specified condition, to perform first authentication of the user by using first biometric information obtained through the biometric sensor, and in the case where the context information satisfies a second specified condition, to perform second authentication of the user by using the first biometric information and the second biometric information obtained through the biometric sensor.

The context information may one of information about whether the electronic device is in an indoor environment or information about whether the electronic device is in an outdoor environment.

The processor may be configured to perform user authentication based on the at least part of the face image and the iris image, in the case where the environment in which the image is obtained is an outdoor environment, as a part of the second specified condition.

The processor may be configured to determine that the context information associated with a capture distance from the biometric sensor is a part of a condition, and to perform user authentication based on the face image and the iris image in the case where the environment in which the image is obtained is a long distance environment (a second specified condition).

An electronic device according to an embodiment of the disclosure may include a biometric sensor including a light emitting unit emitting light of an infrared wavelength band and an infrared camera obtaining an image based on the light of the infrared wavelength band, a memory storing data, which is compared with images obtained based on the biometric sensor, and a processor operatively connected to the biometric sensor and the memory. The processor may be configured to obtain an iris image by using the biometric sensor, to detect an iris difference value by comparing with pre-stored iris information, in the case where the iris difference value is not less than a first threshold value, to determine whether at least one of an external illuminance value or a distance value between a subject and the biometric sensor satisfies a specified condition, and in the case where at least one of the external illuminance value or the distance value satisfies the specified condition, to perform user authentication based on at least part of a face image in an image that the biometric sensor obtains and the iris difference value.

The processor may be configured to determine whether the external illuminance value corresponds to an illuminance value indicating an outdoor environment, or to determine whether the distance value indicates an environment of a long distance of a specified distance or more, and, in the case where a capture environment of the biometric sensor is at least one environment of the outdoor environment and the long distance environment, to perform user authentication based on the at least part of the face image and the iris difference value, in association with the specified condition.

The processor may automatically perform complex authentication, if authentication based on an iris difference value fails, without verifying a condition associated with an outdoor environment, a long distance environment, or the like. The processor may obtain at least one iris image by a specified frequency or more or during a specified time while performing authentication based on the iris difference value, and may perform iris-only authentication on the obtained iris image. In addition, while performing the complex authentication, the processor may perform the complex authentication based on at least one iris difference value and at least one face difference value associated with at least one iris image and at least one face image (or a plurality of iris images and a plurality of face images). If performing complex authentication based on a plurality of iris difference values and a plurality of face difference values, the processor may determine whether authentication is successful, based on an average of each of difference values or may determine whether authentication is successful, based on at least one difference value obtained depending on a specified sampling condition.

The processor may be configured to determine that authentication fails, in the case where the iris difference value is not less than a second threshold value. The electronic device may be operated based on only one threshold value associated with the iris difference value. In this case, the processor may be configured to automatically perform complex authentication in a condition that the iris difference value is not less than the one threshold value.

Figure 6A:
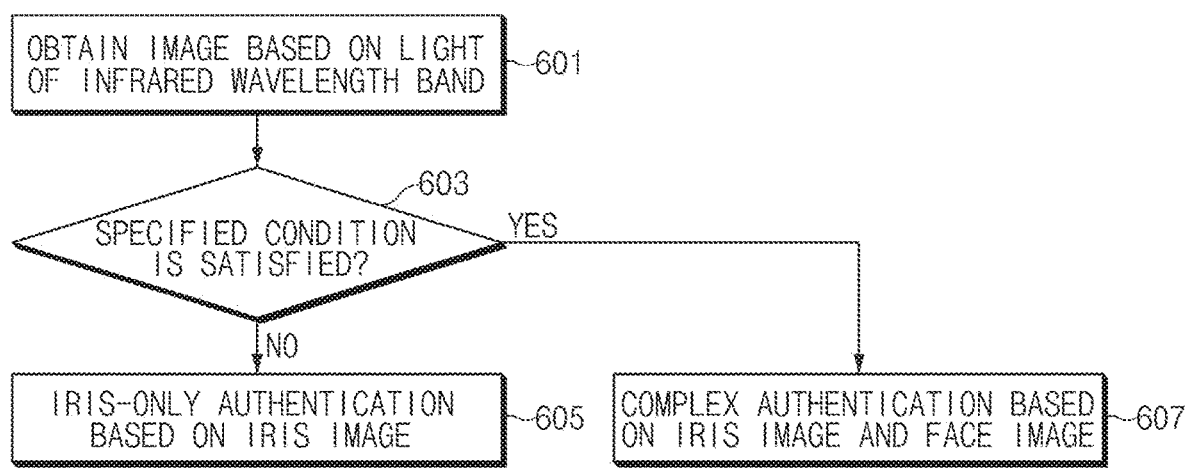
FIG. 6A is a flowchart illustrating an example of an iris-based authentication method according to an embodiment of the disclosure.

FIG. 6A is a flowchart illustrating an example of an iris-based authentication method according to an embodiment of the disclosure.

Referring to FIG. 6A, according to an embodiment of the disclosure, with regard to an iris-based authentication method, in operation 601, the processor 120 may perform an operation of obtaining an image based on the light of an infrared wavelength band. In this regard, the processor 120 may activate a biometric sensor (e.g., an iris sensor) and may obtain an infrared light-based image associated with a subject. In this operation, the processor 120 may obtain at least one of an iris image and a face image.

In operation 603, the processor 120 may determine whether a specified condition is satisfied. For example, the specified condition may include at least one of the condition that an iris difference value is within a first range (e.g., a range in which the iris difference value is greater than a specified first threshold value and is less than a second threshold value greater than the first threshold value), the condition that an external illuminance value is not less than a specified value, or the condition that a distance from the subject is not less than a specified distance. In the case where the iris difference value is not less than the second threshold value, the processor 120 may determine that the authentication fails, without performing complex authentication. With regard to the detection of the distance from the subject, the processor 120 may activate a proximity sensor or a TOF sensor and may calculate the distance from the subject based on the proximity sensor or the TOF sensor. Alternatively, the processor 120 may estimate or calculate the distance from the subject based on at least one (e.g., at least one of an iris size and a face size) of the obtained iris image or face image. Even though the external illuminance value is less than a specified value (e.g., an indoor environment of a specified illuminance), in the case where the distance from the subject is not less than a specified distance, the processor 120 may determine that the condition for complex authentication is satisfied. Even though the distance from the subject is less than a specified value, in the case where the external illuminance value is not less than the specified value (e.g., an outdoor environment of a specified illuminance or more), the processor 120 may determine that the condition for complex authentication is satisfied.

In the case where the external illuminance value is out of an illuminance range capable of performing image-based authentication, the processor 120 may determine that authentication fails, regardless of the distance from the subject; in the case where the distance from the subject is beyond the distance capable of performing image-based authentication (in the case where the distance from the subject is closer than the minimum distance reference value or is farther than the maximum distance reference value), the processor 120 may determine that the authentication fails, regardless of the external illuminance value.

In the case where the specified condition is not satisfied in operation 603, in operation 605, the processor 120 may perform iris image-based iris-only authentication. For example, in the case where the iris difference value is less than the first threshold value, the processor 120 may perform iris-only authentication. In the case where the specified condition is satisfied in operation 603, in operation 607, the processor 120 may perform complex authentication based on an iris image and a face image.

As described above, an iris image-based authentication method according to an embodiment of the disclosure may include an operation of determining whether a specified condition is satisfied, and an operation of performing iris image-based user authentication depending on the satisfaction of the specified condition or performing user authentication based on a face and an iris image.

An iris image-based authentication method according to an embodiment of the disclosure may include an operation of obtaining first biometric information corresponding to a partial area of a subject, an operation of performing first authentication at a first level based on the first biometric information, an operation of determining whether the first authentication satisfies a first specified condition, an operation of executing a specified function in the case where the first authentication satisfies the specified condition, and an operation of performing second authentication on an external object at a second level by using the first biometric information and second biometric information in the case where the first authentication satisfies a second specified condition.

In the above-described operation, the operation of obtaining the first biometric information may include an operation in which the processor 120 obtains an image corresponding to a partial area (e.g., an iris area) associated with the external object by using a biometric sensor.

In the above-described operation, the first authentication may be performed based on the obtained first biometric information (e.g., iris information) at the first level. The operation of performing the first authentication at the first level may be determined by a first threshold value associated with an iris difference value. For example, the first threshold value may be a reference for determining whether to perform iris-only authentication based on an iris difference value between the pre-stored iris template and the currently obtained iris template or whether to perform complex authentication based on the face difference value and the iris difference value. Alternatively, the first threshold value may be determined at the time of security performance settings and may be adjusted depending on the change of user settings. In the case where the obtained first biometric information (e.g., iris difference value) is less than the first threshold value (e.g., in the case where the difference value between the pre-stored iris template and the currently obtained iris template is less than the first threshold value), the processor 120 may determine that the currently obtained iris template is similar to the pre-stored iris template by a reference value or more and may determine that iris authentication is successful.

In the case where the first authentication satisfies a first specified condition (e.g., in the case where the authentication is successful), the processor 120 may execute a specified function. For example, upon the authentication success, the processor 120 may execute a preset function (e.g., account transfer, unlock, or the like). In the case where the first authentication satisfies a second specified condition (e.g., in the case where the authentication fails), the processor 120 may perform second authentication at a second level by using the first biometric information and the second biometric information, which is obtained by using the biometric sensor and which corresponds to another area (e.g., a partial area of a face, an eyebrow, or the like) of the external object. The authentication may be processed depending on the iris difference value and the face difference value in FIG. 4 at the second level.

With regard to the second authentication of the second level, in the case where the iris difference value is not less than a first threshold value associated with iris-only authentication, the processor 120 may determine whether the authentication is successful, depending on the face difference value. In a state where the iris difference value is not less than the first threshold value associated with the iris-only authentication, in the case where the face difference value is relatively small even though the iris difference value is relatively great, the processor 120 may determine that the complex authentication is successful. In this operation, in the case where the processor 120 applies a specific reference value associated with the iris difference value for complex authentication and then the iris difference value is great by the specific reference value or more (or in the case where iris templates are different from each other by a reference value or more, or in the case where the iris difference value is not less than a second threshold value), the processor 120 may determine that the complex authentication fails, regardless of the face difference value.

Figure 6B:
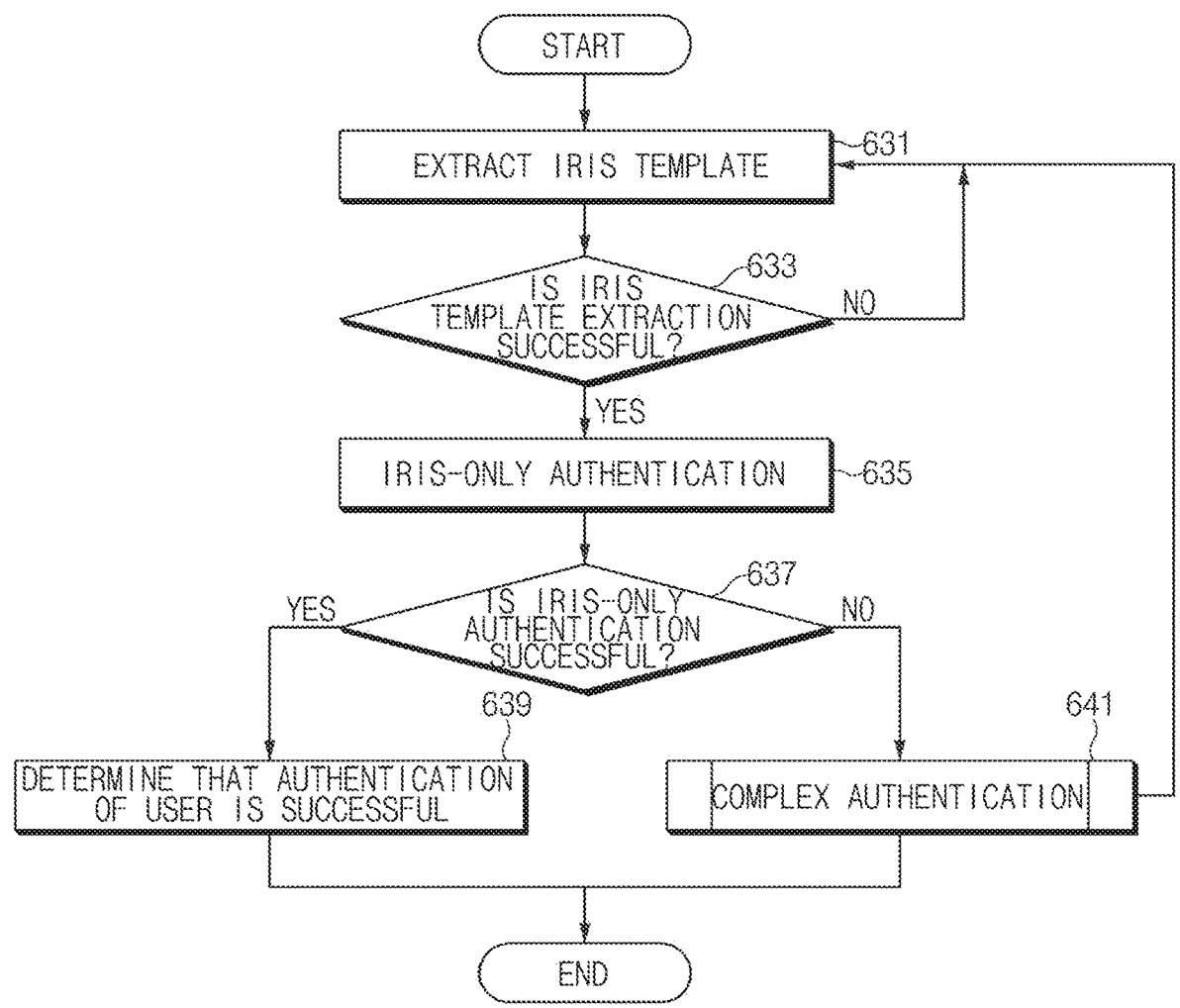
FIG. 6B is a flowchart illustrating another example of an iris-based authentication method according to an embodiment of the disclosure.

FIG. 6B is a flowchart illustrating another example of an iris-based authentication method according to an embodiment of the disclosure.

Referring to FIG. 6B, with regard to an iris-based authentication method according to an embodiment of the disclosure, in operation 631, the processor 120 may try iris template extraction. With regard to this operation, the processor 120 may emit light (e.g., infrared light) of a specified wavelength band, by operating the light emitting unit 131 of the iris sensor 130 and may obtain an IR image (or an infrared capture image) by using the iris camera 132. The processor 120 may detect an iris image from the obtained IR image and may extract an iris template from the detected iris image. The iris template may include information obtained by converting minutiae information of an iris image into a digital code that the electronic device 100 is capable of recognizing.

In operation 633, the processor 120 may determine whether the iris template extraction is successful. In the case where the iris template extraction fails, the processor 120 may try the iris template extraction while branching to operation 631 for a specified frequency. In the case where the specified frequency elapsed, the processor 120 may determine that the iris authentication fails and then may execute a function (e.g., an iris authentication failure guide, the deactivation of the iris sensor 130, or the like). When the iris template extraction fails, the processor 120 may output a guide including at least one of an image or a text for requesting of adjusting the capture angle, a capture distance, or the like of a user's face.

In the case where the iris template extraction is successful, in operation 635, the processor 120 may perform processing associated with iris-only authentication. For example, the processor 120 may compare the extracted iris template with a reference iris template pre-stored in the memory 140 and may determine whether the iris difference value is less than a reference value (e.g., a first threshold value). The processor 120 may compare each of a plurality of pre-stored iris templates with the currently obtained iris template and may determine whether a specified condition is satisfied.

In operation 637, the processor 120 may determine whether the iris-only authentication is successful. If the iris-only authentication is successful, in operation 639, the processor 120 may determine that the authentication of the user is successful. In this operation, the processor 120 may end the iris authentication function and may execute a specified function according to authentication success. For example, the processor 120 may unlock a lock screen or may execute a program, the security function of which is set, depending on the iris authentication success. Alternatively, the processor 120 may read a specified file or may transmit a file, depending on the iris authentication success.

In the case where the iris-only authentication fails, in operation 641, the processor 120 may perform complex authentication. The processor 120 may verify the execution result of the complex authentication and may execute a specified function according to the authentication success if the complex authentication is successful. Alternatively, in the case where the complex authentication fails, the processor 120 may branch to an operation before operation 601 and may repeat the following operation for a specified frequency. The processor 120 may perform complex authentication based on the critical value of iris-only authentication failure. For example, in the case where the iris difference value is not less than the above-described second threshold value (e.g., the iris image of another person), the processor 120 may determine that the authentication fails, without performing the complex authentication.

With regard to the complex authentication, the processor 120 may compare the current face template and current iris template, which are extracted from a face image and an iris image captured based on the infrared light, with the pre-stored face template and iris template. In the case where each of a face difference value (a difference between the pre-stored face template with the currently obtained face template, as the difference value decreases, the similarity increases) and an iris difference value (a difference between the pre-stored iris template and the currently obtained iris template, as the difference value decreases, the similarity increases) is less than a reference value set to determine whether complex authentication is successful, the processor 120 may determine that the complex authentication is successful. With regard to the performing of the complex authentication, the processor 120 may extract a face template from the obtained infrared-based face image and may compare the extracted face image with the pre-stored face template. In this operation, the processor 120 may determine a type of the face image (e.g., whether the obtained face image is the entire face image or which portion of a partial face image is matched to the obtained face image) obtained based on the minutiae extraction and the comparison with the pre-stored database. The processor 120 may collect a face template corresponding to at least part of face image to be compared, depending on the determined type of a face image and may compare the collected face template with the currently obtained face template.

As described above, one method of an iris-based authentication according to an embodiment of the disclosure may perform iris-only authentication and then may perform complex authentication if the iris-only authentication fails.

Figure 7:
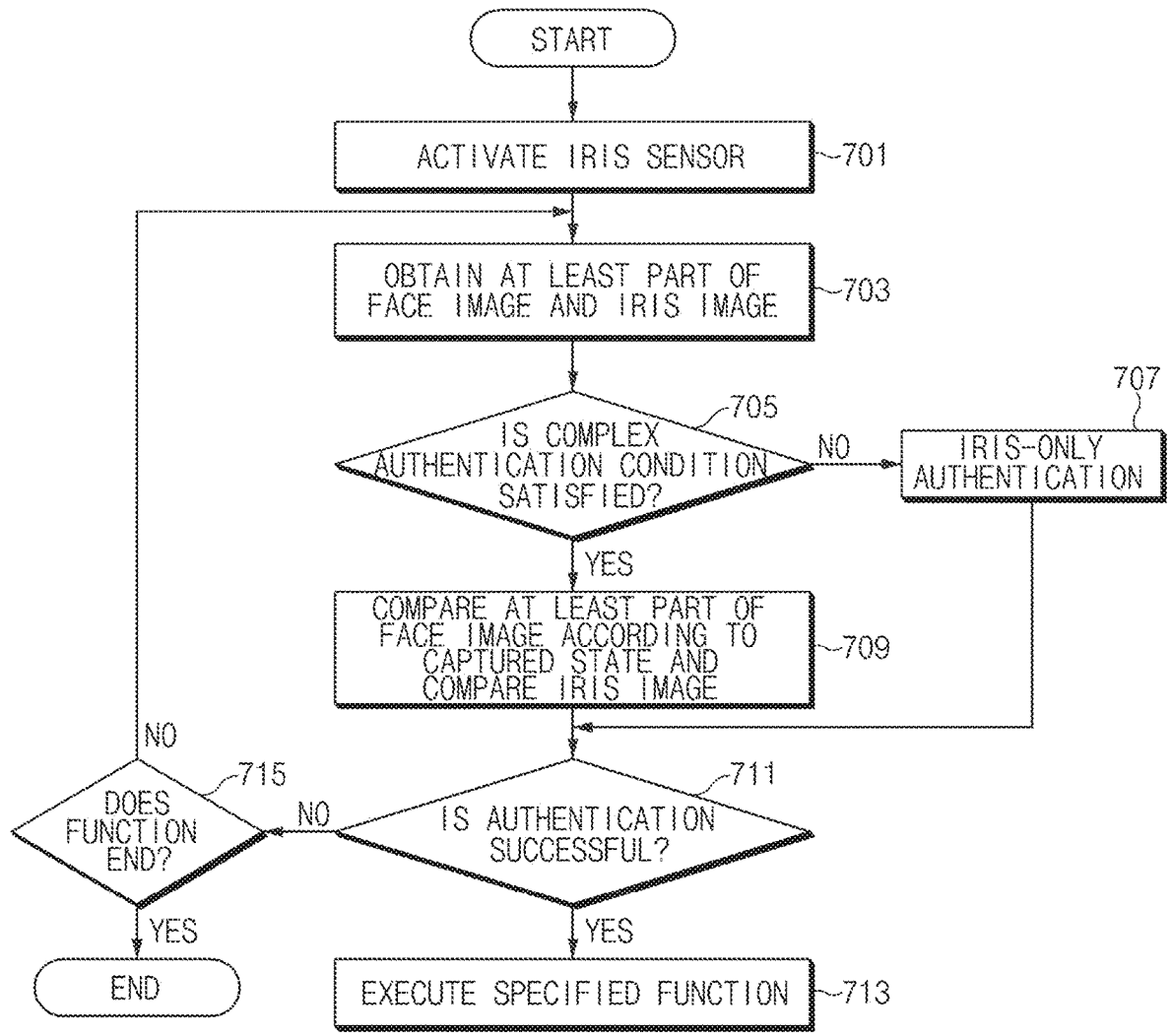
FIG. 7 is a flowchart illustrating another example of an iris-based authentication method according to an embodiment of the disclosure.

FIG. 7 is a flowchart illustrating another example of an iris-based authentication method according to an embodiment of the disclosure.

Referring to FIG. 7, with regard to an iris-based authentication method according to an embodiment of the disclosure, in operation 701, the processor 120 may activate the iris sensor 130. The processor 120 may activate the light emitting unit 131 and may control the light emitting unit 131 to emit the light of a specified wavelength band. The processor 120 may supply power to the iris camera 132 and may allow the iris camera 132 to capture an infrared-based image.

In operation 703, the processor 120 may obtain at least part of a face image and an iris image based on infrared light by using the iris camera 132. If a specified condition is satisfied, the processor 120 may obtain the infrared-based face image and iris image. For example, while the processor 120 obtains an IR preview image, in the case where the size of the obtained face image is not less than a specified size, the processor 120 may automatically obtain an IR still image. Alternatively, while the processor 120 obtains an IR preview image, in the case where the size of an iris is not less than a specified size or the distance between two eyes is not less than a specified distance (as the distance between two eyes increases, the distance from two eyes is determined as the short distance, and as the distance between two eyes decreases, the distance from two eyes is determined as the long distance. Accordingly, if the distance between two eyes is not less than a specific distance, it is determined that iris-only authentication or complex authentication is possible), the processor 120 may automatically obtain an IR still image. The processor 120 may obtain the infrared-based face image and iris image in response to a user input. With regard to the obtaining of at least part of face image and an iris image, the processor 120 may output a guide including at least one of an image or a text for requesting of the adjustment of the face direction of a user or the distance between the user's face and the iris camera 132.

In operation 705, the processor 120 may determine whether a complex authentication condition is satisfied. For example, the processor 120 may determine whether the complex authentication condition is satisfied, based on at least one of the calculation of the distance from the subject and indoor/outdoor determination. In the case where the distance from the subject is within a first range (or in the case where the distance from the subject is not less than a specified distance) or in the case where the current environment is an outdoor environment, the processor 120 may determine that the complex authentication condition is satisfied. In this regard, in the case where the size of an iris is not greater than a specified size or in the case where the distance between two eyes is not greater than a specified size, the processor 120 may determine that the complex authentication condition is satisfied. The processor 120 may verify external illuminance by using an illuminance sensor, may determine that the current environment is an outdoor environment in the case where the external illuminance is not less than a specified value, and determine that the complex authentication condition is satisfied, based on the determined result.

The processor 120 may determine whether a complex authentication score including an iris difference value and a face difference value is less than a specified value. In this regard, if the iris difference value is not less than a first threshold value (a reference value for performing iris-only authentication), the processor 120 may obtain the face difference value and may determine whether a condition for performing the complex authentication that is based on the obtained iris difference value and face difference value is satisfied. In the case where the authentication of a user succeeds by using information extracted based on an iris, the processor 120 may not perform additional complex authentication. However, in the case where the authentication of a user fails by using information extracted based on an iris, the processor 120 may perform complex authentication with additional information (e.g., information based on a part of a face) and iris information for the purpose of reducing FRR.

In the case where the complex authentication condition is not satisfied, in operation 707, the processor 120 may perform iris-only authentication. For example, the processor 120 may extract an iris template based on an iris image and may not perform the comparison of a face difference value but perform iris-only authentication in the case where the iris difference value calculated by using the extracted iris template is less than a specified value (e.g., the first threshold value). The processor 120 may verify a value of an iris size or a distance value between two eyes and may perform iris-only authentication in the case where the value of the iris size is not less than a specified size or in the case where the distance value between two eyes is not less than a specified distance. Alternatively, in the case where an external illuminance value is intensity determined as an indoor environment (or is in an indoor environment), the processor 120 may perform iris-only authentication.

In the case where the complex authentication condition is satisfied, in operation 709, the processor 120 may perform at least part of comparison of a face image according to the captured state and iris image comparison. In this operation, the processor 120 may perform iris template comparison and face template comparison.

In operation 711, the processor 120 may determine whether the authentication is successful. In the case where the authentication is successful, in operation 713, the processor 120 may execute a specified function according to the authentication success. For example, the processor 120 may unlock a lock screen, may obtain a voice command, and may execute a function according to the obtained voice command, depending on the authentication success. Alternatively, the processor 120 may execute an application, the security function of which is set, depending on the authentication success.

In the case where the authentication fails, in operation 715, the processor 120 may determine whether an iris-based authentication function ends. If an event associated with the end of the iris-based authentication function does not occur, the processor 120 may return to operation 703 and may perform the following operations again. If an event associated with the end of the iris-based authentication function occurs, the processor may end the iris-based authentication function.

Figure 8:
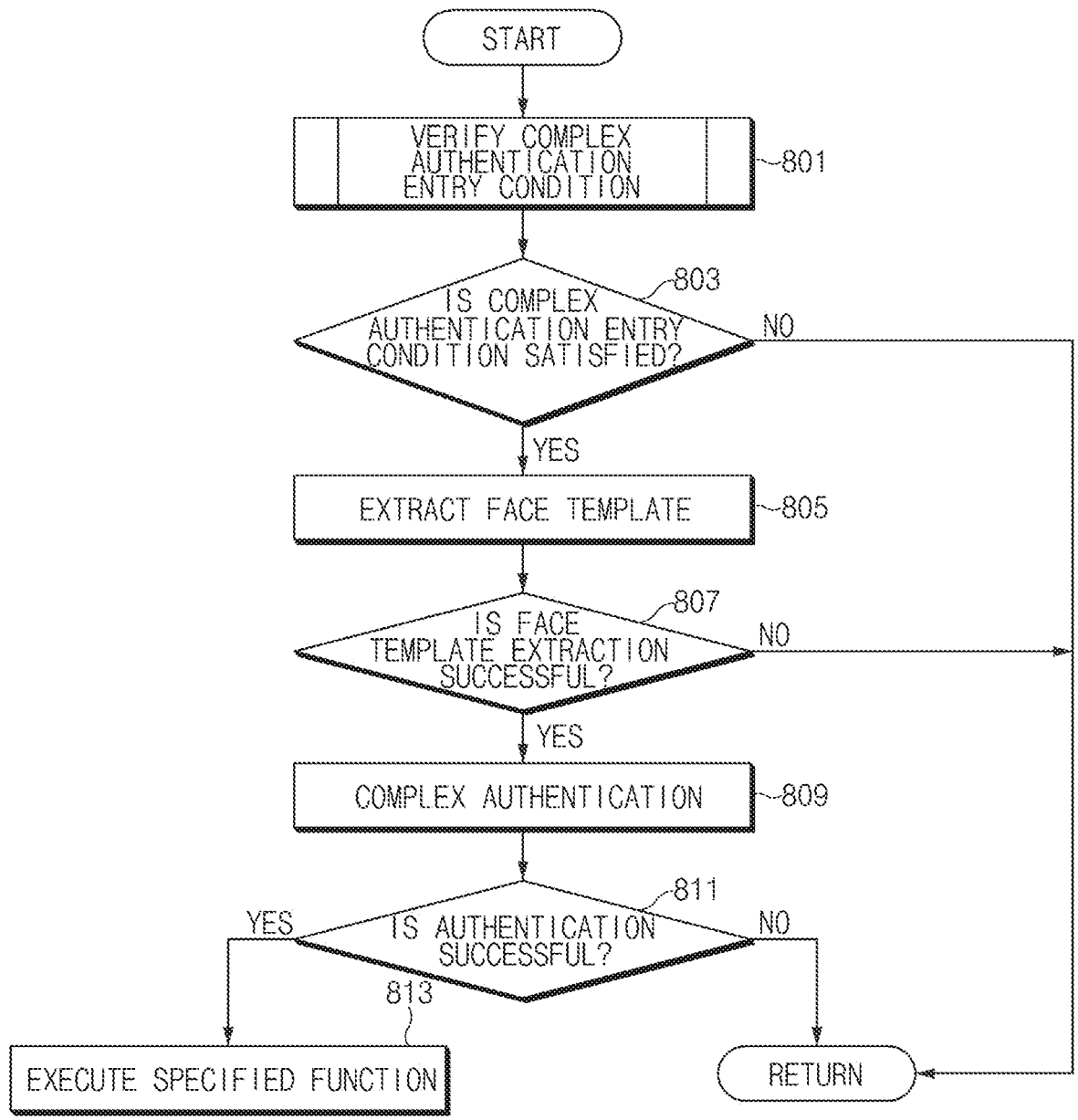
FIG. 8 is a flowchart illustrating an example of a complex authentication method among iris-based authentication methods according to an embodiment of the disclosure.

FIG. 8 is a flowchart illustrating an example of a complex authentication method among iris-based authentication methods according to an embodiment of the disclosure.

Referring to FIG. 8, with regard to a complex authentication method according to an embodiment of the disclosure, in operation 801, the processor 120 may verify a complex authentication entry condition. For example, the complex authentication entry condition may include a condition for determining whether the current environment is an indoor environment or an outdoor environment. For example, the complex authentication entry condition may include a condition for determining whether the current environment is a long distance environment or a short distance environment. In this regard, the processor 120 may measure an illuminance value or light intensity by using an illuminance sensor, an RGB camera, or the like. In the case where the illuminance value is less than a specified value, the processor 120 may determine that the current environment is an indoor environment; in the case where the illuminance value is not less than a specified value, the processor 120 may determine that the current environment is an outdoor environment. The processor 120 may verify parameters according to an operating environment of the iris sensor 130 to determine whether the current environment is an indoor environment or an outdoor environment. In association with the verification of the long distance environment, the processor 120 may calculate a spaced distance between a subject and the electronic device 100 by using a proximity sensor or a TOF sensor. Alternatively, the processor 120 may verify the size of a face image (or an iris) obtained based on the iris camera 132, and in the case where the size is not greater than a specified size, the processor 120 may determine that the current environment is a long distance environment. The processor 120 may obtain the voice of a user by using a plurality of microphones, and after calculating a spaced distance between the user's face and the electronic device 100 based on a plurality of microphones, the processor 120 may determine that the current environment is a long distance environment, depending on the calculated spaced distance.

In operation 803, the processor 120 may determine whether the complex authentication entry condition is satisfied. For example, the processor 120 may determine whether at least one of the verified various elements satisfies the preset complex authentication entry condition. For example, in the case where the current environment is an outdoor environment, the processor 120 may determine that the complex authentication entry condition is satisfied. In the case where the current environment is a long distance environment, the processor 120 may determine that the complex authentication entry condition is satisfied. In the case where the current environment is an outdoor environment and a first long distance environment, the processor 120 may determine that the complex authentication entry condition is satisfied. In the case where the current environment is an indoor environment and a second long distance environment (e.g., in the case where the subject is farther away from the electronic device 100 than the first long distance environment), the processor 120 may determine that the complex authentication entry condition is satisfied.

If the complex authentication entry condition is satisfied, in operation 805, the processor 120 may try to extract a face template. In this operation, the processor 120 may extract a face template by using at least part of a face image obtained based on infrared light. For example, the processor 120 may extract the face template associated with the entire face image or may extract the face template associated with a partial face image. In the case where the entire face image is not obtained from an image captured based on the iris camera 132, the processor 120 may extract the face template, based on the partial face image. The processor 120 may extract the face template of a specified portion (e.g., a left eye portion, a right eye portion, a first center part including two eyes centered on the middle of the forehead, or a second center part including the middle of the forehead, two eyes, and two ears) in the partial face image depending on user settings. For example, the specified portion may be changed depending on the complex authentication condition. In the case where the current environment is the indoor environment and the second long distance environment, the processor 120 may extract a face template associated with the entire face or a face template corresponding to the first the center part or the second the center part. In the case where the current environment is the outdoor environment and the first long distance environment, the processor 120 may extract a face template of at least one of the left eye portion, the right eye portion, or the first center part. The processor 120 may differently determine a type of a function executed through iris authentication or the specified portion depending on security level. For example, when executing an application of a relatively high security level (e.g., a function execution request associated with financial information processing), the processor 120 may extract the face template of the relatively detailed face portion (e.g., the left eye portion, the right eye portion, the first center part, or the like). When executing an application of a relatively low security level (e.g., a request for unlocking a lock screen), the processor 120 may extract the face template of a relatively rough face portion (e.g., the second center part, the entire face, or the like).

In operation 807, the processor 120 may determine whether the face template extraction is successful. In the case where the face template extraction is successful, in operation 809, the processor 120 may perform complex authentication. As described above, the complex authentication may include an operation of comparing the iris template obtained from an iris image and the face template obtained in operation 805 with the pre-stored iris template and the pre-stored face template. In this operation, the processor 120 may collect the pre-stored face template corresponding to the obtained face portion from the memory 140.

In operation 811, the processor 120 may determine whether complex authentication is successful. If the complex authentication is successful, in operation 813, the processor 120 may execute a specified function according to the authentication success. The electronic device 100 may differently provide the limit ranges of a function executed upon iris-only authentication and a function executed upon complex authentication. For example, in the case where the authentication of a user is successful depending on the performing of the iris-only authentication, the processor 120 may allow the user to access a function of a relatively high security level or the area of the memory 140 in which data of a relatively high security level is stored. In the case where the authentication of a user is successful depending on the performing of the complex authentication, the processor 120 may allow the user to access a function of a relatively low security level or the area of the memory 140 in which data of a relatively low security level is stored. In association with the viewing of photos stored in a gallery app, upon iris-only authentication success, the processor 120 may support the viewing of the stored entire photos and may support the viewing of some of all the photos upon complex authentication success. The processor 120 may support a web surfing function and an email writing function upon iris-only authentication success and may not support the email writing function but support only the web surfing function upon complex authentication success. The security level settings associated with the complex authentication and iris-only authentication may be changed depending on user settings. In this case, the access to the function of a relatively high security level may be allowed depending on the performing of complex authentication. Alternatively, the access to the function of a relatively low security level may be allowed depending on the performing of iris-only authentication.

For example, if the complex authentication fails, the processor 120 may return to a specified operation. With regard to the return to the specified operation, the processor 120 may return to operation 801 and may perform the following operation by a specified frequency.

Figure 9:
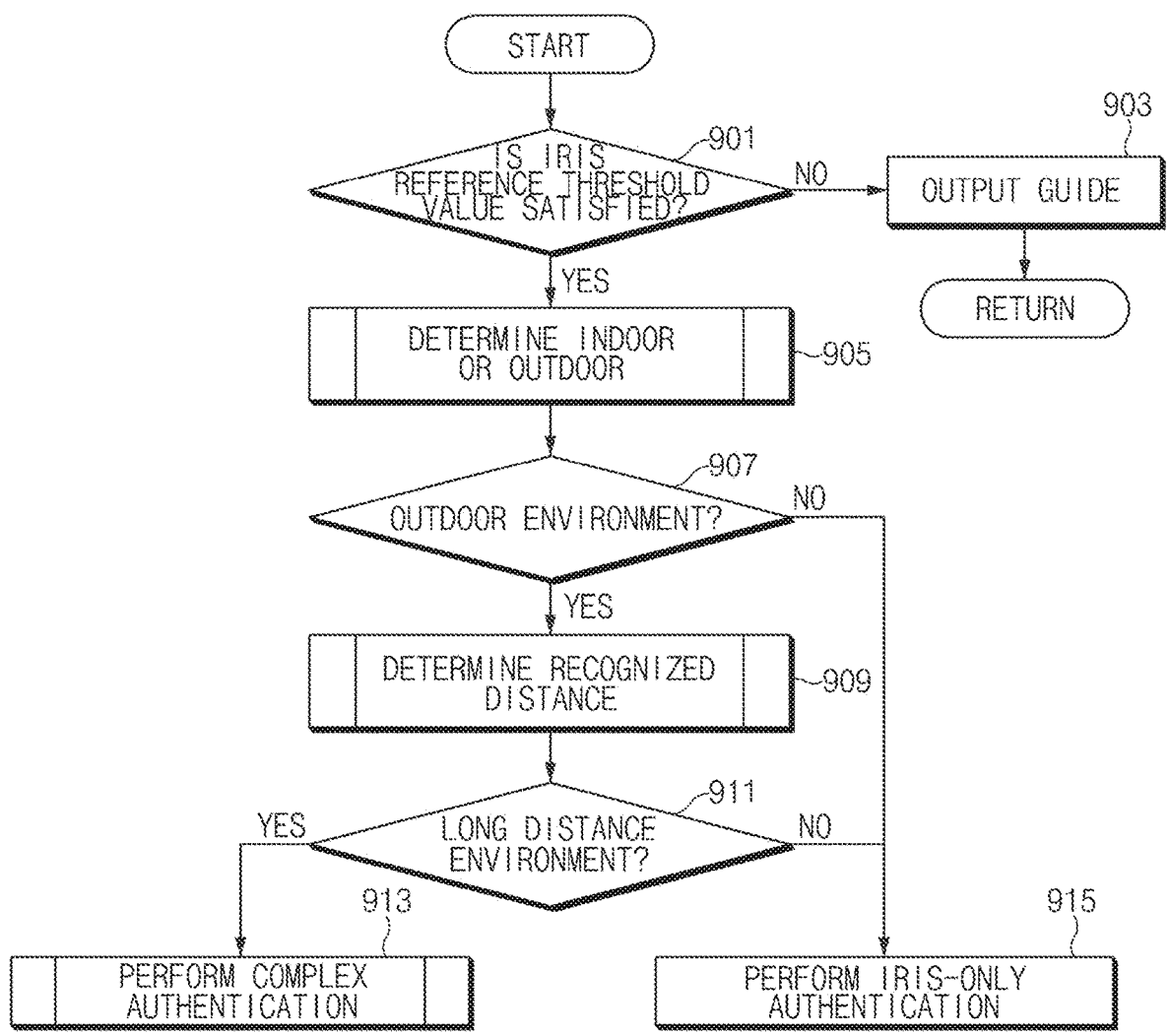
FIG. 9 is a flowchart illustrating an example of a complex authentication performing method according to an embodiment of the disclosure.

FIG. 9 is a flowchart illustrating an example of a complex authentication performing method according to an embodiment of the disclosure.

Referring to FIG. 9, with regard to the complex authentication performing method, in operation 901, the processor 120 may determine whether an iris reference threshold value condition is satisfied. For example, the processor 120 may determine whether a difference between the pre-stored iris template and an iris template extracted from the currently obtained iris image is not greater than a reference threshold value.

In the case where the iris reference threshold value is not less than a preset value, in operation 903, the processor 120 may output a guide. The guide may include at least part of an image or a text for requesting to move a user's face in a specified direction. After outputting the guide, the processor 120 may return to operation 901. In the case where the iris reference threshold value is not satisfied during a specified time, the processor 120 may end an iris authentication function.

In the case where the iris reference threshold value condition is satisfied, in operation 905, the processor 120 may perform indoor or outdoor determination. As described below with reference to FIG. 11, the indoor or outdoor determination may be performed through an ambient light condition and pieces of information associated with the parameter of the iris camera 132.

In operation 907, the processor 120 may determine whether the current environment is an outdoor environment. In the case where the current environment is the outdoor environment, in operation 909, the processor 120 may perform recognized distance determination. As described below with reference to FIG. 12 or 13, the recognized distance determination may be performed based on the size of an iris, a distance between two eyes, or the like.

In operation 911, the processor 120 may determine whether the current environment is a long distance environment. In the case where the current environment is the long distance environment, in operation 913, the processor 120 may perform complex authentication. In the case where the current environment is not the long distance environment, in operation 915, the processor 120 may perform iris-only authentication. In operation 907, in the case where the current environment is not the outdoor environment (in the case where the current environment is the indoor environment), the processor 120 may perform iris-only authentication in operation 915.

The processor 120 may determine an indoor/outdoor condition and a long distance condition to perform complex authentication. For example, even though the indoor environment is within a specified illuminance value, in the case where the distance from the subject is within a specified range (or is not less than a specified distance), the processor 120 may perform complex authentication. In the above-described operation, the operation of determining an indoor/outdoor environment and an operation of determining a long distance environment may be performed regardless of an order or at the same time.

Figure 10:
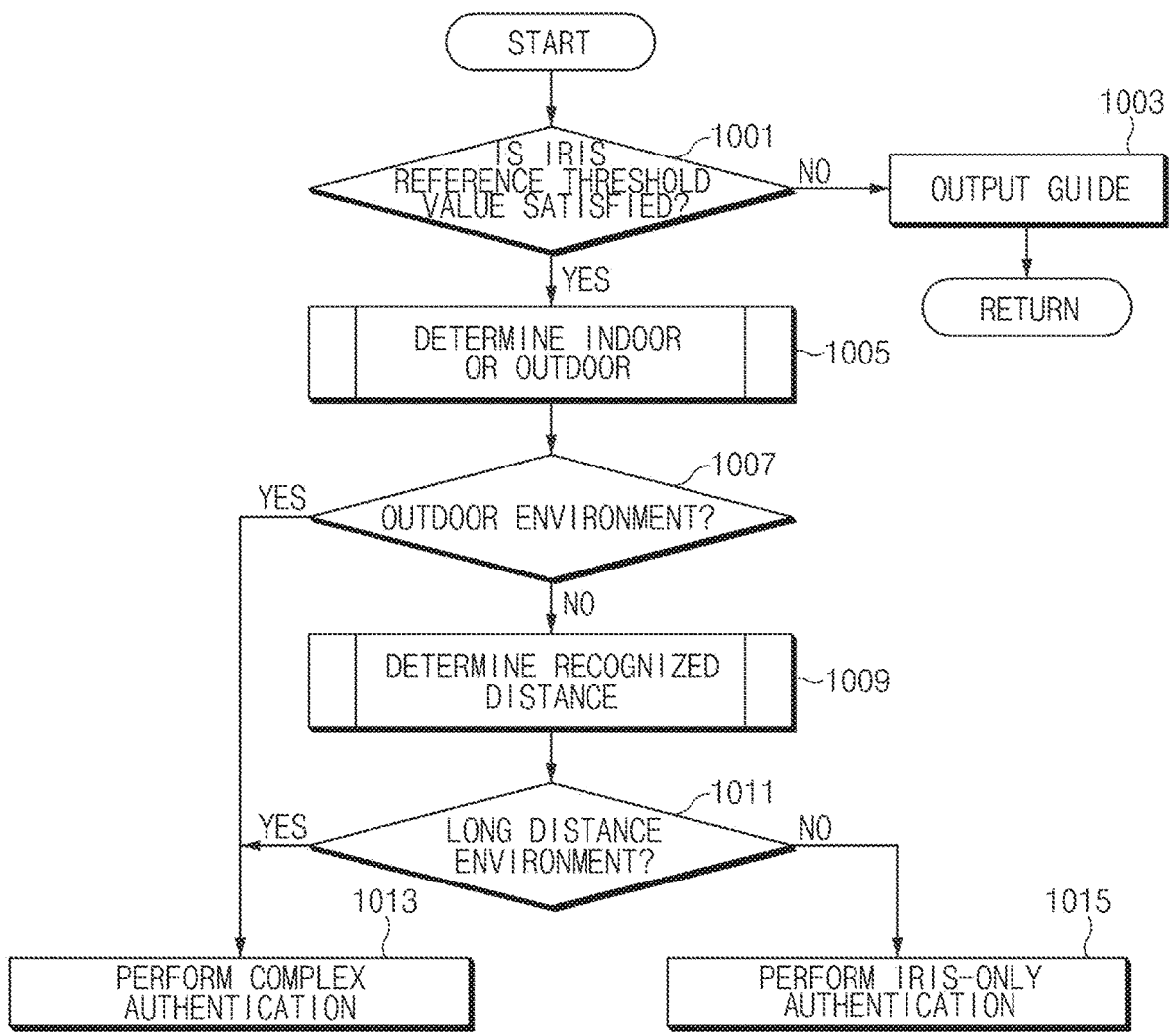
FIG. 10 is a flowchart illustrating another example of a complex authentication performing method according to an embodiment of the disclosure.

FIG. 10 is a flowchart illustrating another example of a complex authentication performing method according to an embodiment of the disclosure.

Referring to FIG. 10, with regard to the complex authentication performing method, in operation 1001, the processor 120 may determine whether an iris reference threshold value condition is satisfied. In the case where the iris reference threshold value condition is not satisfied, in operation 1003, the processor 120 may output a guide. For example, the guide may include at least part of an image or a text for requesting to adjust the spaced distance between a user and the electronic device 100 or a location at which a user's face is captured by the iris camera 132. After outputting the guide, the processor 120 may return to a specified operation. For example, the processor 120 may branch to an operation before operation 1001 to again determine whether the iris reference threshold value condition is satisfied. The processor 120 may determine whether an iris authentication function ends, and in the case where an event associated with the end of the iris function does not occur, the processor 120 may branch to an operation before operation 1001 and may perform the following operation again.

In the case where the iris reference threshold value condition is satisfied, in operation 1005, the processor 120 may perform indoor or outdoor determination. In this regard, the processor 120 may collect various sensor information or information (e.g., the setting parameter value of an iris camera or a light emitting unit, or the like) about the element of an electronic device, for indoor or outdoor determination. The processor 120 may compare the collected information about the element with the pre-stored reference information and may determine whether the current environment is an indoor environment or an outdoor environment, as described in operation 1007.

In the case where the current environment is not the outdoor environment (in the case where the current environment is the indoor environment), in operation 1009, the processor 120 may determine the recognized distance. In this regard, the processor 120 may collect the size information of an iris or a distance value between two eyes.

In operation 1011, the processor 120 may determine whether the current environment is a long distance environment, based on the obtained information. For example, the processor 120 may determine whether an iris size or a distance between two eyes is less than a preset reference value, and in the case where the iris size or the distance between two eyes is less than a preset reference value, the processor 120 may determine that the current environment is a long distance environment. If it is determined that the current environment is the long distance environment, in operation 1013, the processor 120 may perform complex authentication. In the case where the current environment is not the long distance environment (or if the current environment is an environment in which the iris size or the distance between two eyes is less than the preset reference value), in operation 1015, the processor 120 may perform iris-only authentication.

After complex authentication success, the processor 120 may perform a specified first function, and after iris-only authentication success, the processor 120 may perform a specified second function. In the case where the failure occurs in a process of performing iris-only authentication by a specified frequency or more, the processor 120 may automatically perform complex authentication. If complex authentication is successful in an environment in which unlock of a lock screen is requested, the processor 120 may execute a function to unlock a lock screen. If iris-only authentication is successful in an environment in which unlock of a lock screen is requested, the processor 120 may execute at least one set user function (e.g., a function to check a message or an email) together with unlock of a lock screen. If the complex authentication is successful in a voice command function execution environment, the processor 120 may obtain information corresponding to a voice command from an external electronic device and may output the obtained information. If the iris-only authentication is successful in a voice command function execution environment, the processor 120 may obtain information corresponding to a voice command from the memory 140 of the electronic device 100 and may output the obtained information.

The processor 120 may determine the satisfaction of a complex authentication condition, regardless of the order of long distance and indoor/outdoor condition determination. For example, the processor 120 may perform the operation of determining an indoor/outdoor determination after the operation of determining a long distance environment. As such, in the case where the current environment is an outdoor environment, in which the distance from the subject is less than a reference value and the illuminance value of which is not less than a specified illuminance value, the processor 120 may perform complex authentication.

Figure 11:
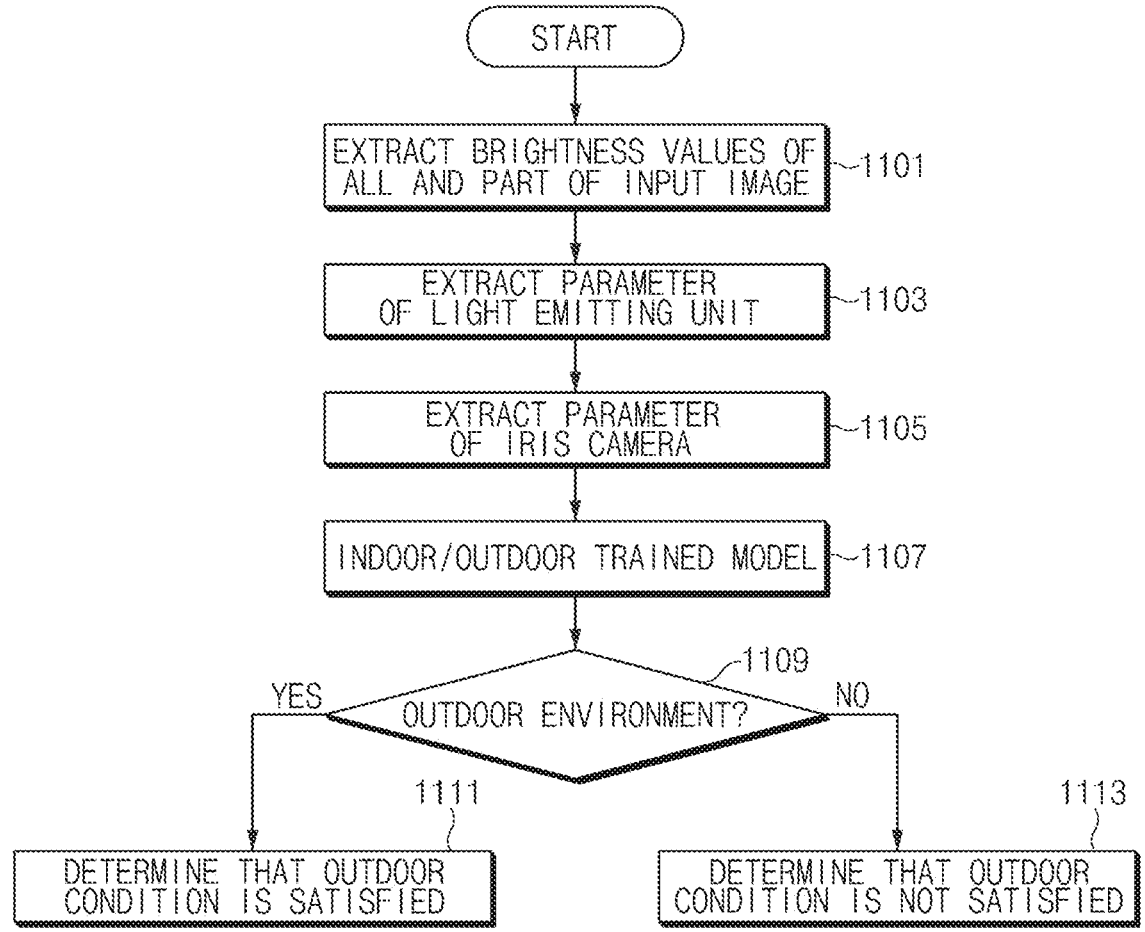
FIG. 11 is a flowchart illustrating an example of an electronic device operating method associated with indoor/outdoor determination according to an embodiment of the disclosure.

FIG. 11 is a flowchart illustrating an example of an electronic device operating method associated with indoor/outdoor determination according to an embodiment of the disclosure.

Referring to FIG. 11, with regard to the electronic device operating method, in operation 1101, the processor 120 (or a processor for iris sensing) may extract the brightness values of the all and part of an input image. With regard to this operation, the processor 120 may operate the iris sensor 130 to obtain, based on infrared light, an input image including at least part of a face image of a subject.

In operation 1103, the processor 120 may extract the parameter of the light emitting unit 131 (e.g., infrared LED). For example, the processor 120 may extract the intensity, the emitting time, the emitting period, the wavelength range information, or the like of the light, which is emitted by the light emitting unit 131, as the parameter of the light emitting unit 131.

In operation 1105, the processor 120 may extract the parameter of the iris camera 132 (or an infrared camera). For example, the processor 120 may extract a parameter associated with the exposure time (e.g., a shutter speed, an aperture size, or the like) of the iris camera 132, a type of the used filter, or the like. An embodiment is above exemplified as the extraction of the parameter of the light emitting unit 131 is performed earlier than the extraction of the parameter of the iris camera 132. However, embodiments of the disclosure may not be limited thereto. For example, the processor 120 may perform the extraction of the parameter of the iris camera 132 earlier than the extraction of the parameter of the light emitting unit 131.

In operation 1107, the processor 120 may generate an indoor/outdoor trained model. For example, the processor 120 may generate a trained model based on the collected parameter associated with the light emitting unit 131 and the collected parameter of the iris camera 132.

In operation 1109, the processor 120 may determine whether the current environment is an outdoor environment, based on the indoor/outdoor trained model. In this regard, the electronic device 100 may store and manage a reference model in which an indoor or outdoor environment is defined. The processor 120 may determine whether the current IR image capture environment is an indoor environment or an outdoor environment, by comparing the trained model generated by using parameters associated with an IR image capture with the pre-stored reference model.

In the case where the comparison result of the generated indoor/outdoor trained model and the pre-stored reference model indicates that a difference between the indoor/outdoor trained model corresponding to an outdoor environment and the reference model is not greater than a reference value (or in the case where similarity is not less than the reference value), in operation 1111, the processor 120 may determine that an outdoor condition is satisfied. Additionally or alternatively, in the case where the current IR image capture environment is the outdoor condition, the processor 120 may execute a function (e.g., a complex authentication function) according to an outdoor condition.

In the case where the comparison result of the generated indoor/outdoor trained model and the pre-stored reference model indicates that a difference between the indoor/outdoor trained model corresponding to an outdoor environment and the reference model is not less than a reference value (or in the case where similarity is not greater than the reference value), in operation 1113, the processor 120 may determine that an outdoor condition is not satisfied. Alternatively, the processor 120 may determine that an indoor condition is satisfied. Additionally or alternatively, in the case where the outdoor condition is not satisfied or in the case where the indoor condition is satisfied, the processor 120 may execute a function (e.g., an iris-only authentication function) according to the indoor condition.

Figure 12:
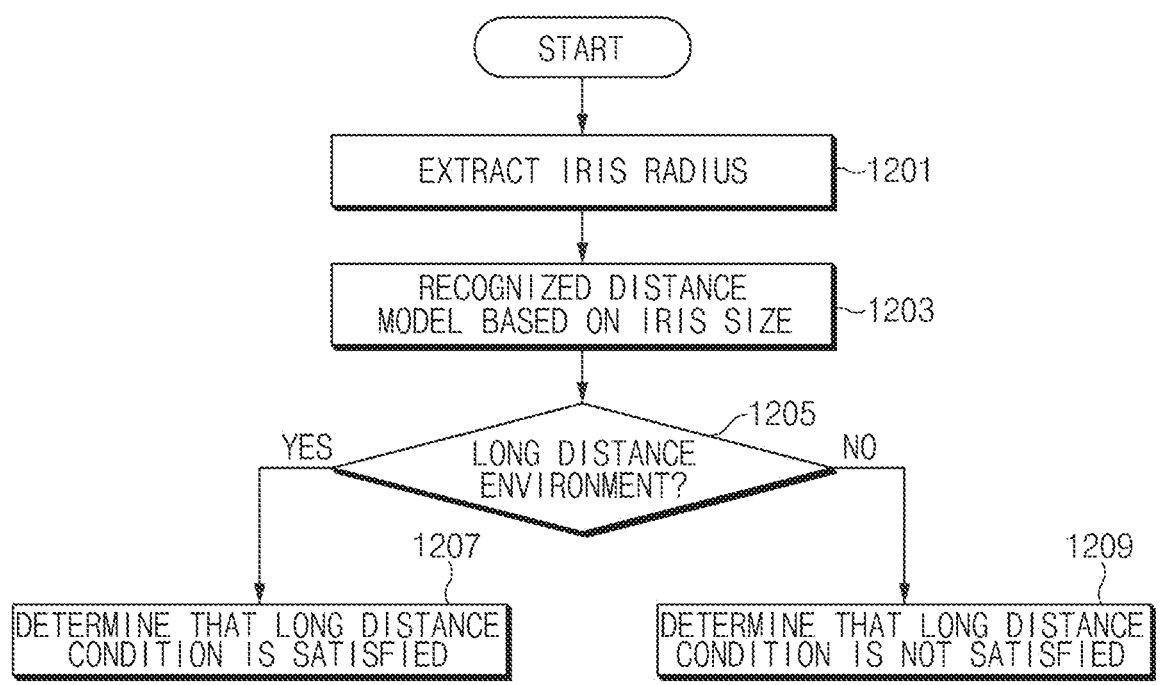
FIG. 12 is a flowchart illustrating an example of an electronic device operating method associated with recognized distance determination according to an embodiment of the disclosure.

FIG. 12 is a flowchart illustrating an example of an electronic device operating method associated with recognized distance determination according to an embodiment of the disclosure.

Referring to FIG. 12, with regard to an electronic device operating method according to an embodiment of the disclosure, in operation 1201, the processor 120 may extract an iris radius. In this regard, the processor 120 may activate the iris sensor 130 and may obtain a subject image based on infrared light, and then the processor 120 may detect an iris image. The processor 120 may obtain an iris image of at least one eye of two eyes and may measure the iris radius in the obtained iris image. The processor 120 may collect information about the size of an iris (e.g., the horizontal diameter of the iris, or the vertical diameter or radius of the iris).

In operation 1203, the processor 120 may generate the iris size-based recognized distance model. The processor 120 may generate a model for generating a distance value between a user and a subject depending on the iris size. The model may include digital code values corresponding to the iris size such that the model is compared with the pre-stored reference model.

In operation 1205, the processor 120 may determine whether the current environment is a long distance environment. In this regard, the processor 120 may compare the generated iris size-based recognized distance model with the pre-stored model. The pre-stored model may include a reference model generated based on an iris image including an iris of a specified size or more. In this regard, the proportional information about the specified iris size and a distance between the user and the electronic device 100 may be stored and managed. The iris size at the maximum distance at which iris-only authentication is capable of being performed may be a reference model of the recognized distance model.

In the case where the currently obtained iris image is a model corresponding to a long distance environment (e.g., in the case where the recognized distance model based on the currently obtained iris size is less than the pre-stored model), in operation 1207, the processor 120 may determine that a long distance condition is satisfied. Additionally or alternatively, if the long distance condition is satisfied, the processor 120 may execute a specified function (e.g., a complex authentication function).

In the case where the currently obtained iris image is a model corresponding to a short distance environment (e.g., in the case where the recognized distance model based on the currently obtained iris size is not less than the pre-stored model), in operation 1209, the processor 120 may determine that a long distance condition is not satisfied. Alternatively, the processor 120 may determine that a short distance condition is satisfied. Additionally or alternatively, if the long distance condition is not satisfied or if the short distance condition is satisfied, the processor 120 may execute a specified function (e.g., an iris-only authentication function). In the case where the recognized distance model based on the currently obtained iris size is less than a specified lower limit value, the processor 120 may determine that the iris recognition function fails, without executing the complex authentication function.

Figure 13:
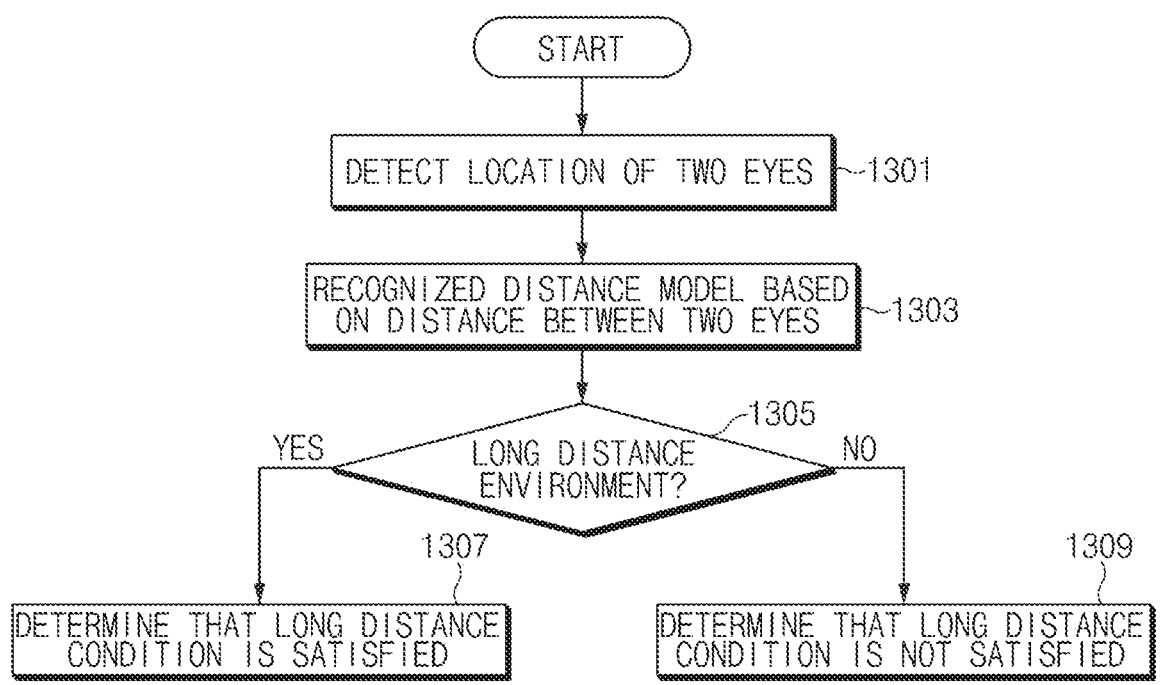
FIG. 13 is a flowchart illustrating another example of an electronic device operating method associated with recognized distance determination according to an embodiment of the disclosure.

FIG. 13 is a flowchart illustrating another example of an electronic device operating method associated with recognized distance determination according to an embodiment of the disclosure.

Referring to FIG. 13, with regard to an electronic device operating method according to an embodiment of the disclosure, in operation 1301, the processor 120 may detect the location of two eyes. In this regard, the processor 120 may activate the iris sensor 130 and may obtain a subject image based on infrared light, and then the processor 120 may obtain an image corresponding to the periphery of eyes. The processor 120 may detect the location of two eyes from the obtained image, based on "eye minutiae". The electronic device 100 may store information about the eye minutiae in the memory 140, and when detecting the location of two eyes, the electronic device 100 may use pieces of information about the eye minutiae stored in the memory 140.

In operation 1303, the processor 120 may generate a recognized distance model that is based on the distance between two eyes. For example, the recognized distance model that is based on the distance between two eyes may include values obtained by converting a feature value corresponding to the distance between two eyes into a digital code such that the recognized distance model that is based on the distance between two eyes is compared with the pre-stored reference model. For example, the pre-stored reference model may include a model corresponding to the distance value between two eyes in a state where iris-only authentication is capable of being performed. In this regard, in a process in which a user registers an iris template, if the face image is obtained depending on guide information in a state where the distance between the user and the electronic device 100 is less than a specific distance, the processor 120 may use the distance value between two eyes in the corresponding face image to generate the reference model.

In operation 1305, the processor 120 may determine whether the current environment is a long distance environment. In this regard, the processor 120 may compare the currently obtained recognized distance model based on the distance between two eyes with the pre-stored reference model. As described above, the pre-stored model may be a model generated based on an image, in which the distance between two eyes is a constant distance, in at least part of a face image captured by using infrared light. When the generated recognized distance model based on the distance between two eyes is compared with the pre-stored model, as the distance between two eyes in the recognized distance model generated based on the currently obtained distance between two eyes is closer than the distance in the reference model, in operation 1307, the processor 120 may determine that a long distance condition is satisfied. Additionally or alternatively, if the long distance condition is satisfied, the processor 120 may execute a specified first function (e.g., the execution of complex authentication and a function according to the execution of complex authentication).

When the generated recognized distance model based on the distance between two eyes is compared with the pre-stored model, in the case where the distance between two eyes in the recognized distance model generated based on the currently obtained distance between two eyes is farther than or the same as the distance in the reference model, in operation 1309, the processor 120 may determine that the long distance condition is not satisfied. Alternatively, the processor 120 may determine that a short distance condition is satisfied. Additionally or alternatively, if the long distance condition is not satisfied or if the short distance condition is satisfied, the processor 120 may execute a specified second function (e.g., the execution of iris-only authentication and a function according to the execution of iris-only authentication). In the case where the distance between two eyes in the recognized distance model based on the currently obtained distance between two eyes is closer than a specified reference value, the processor 120 may determine that the iris recognition function fails, without executing the complex authentication function.

An iris-based authentication method according to an embodiment of the disclosure includes emitting light of an infrared wavelength band and obtaining an image based on the light of the infrared wavelength band, determining whether a specified condition is satisfied, if the specified condition is satisfied, performing user authentication (e.g., complex authentication) based on at least part of a face image and an iris image of the image that a biometric sensor obtains, or, if the specified condition is not satisfied, performing the user authentication (e.g., iris-only authentication) based on the iris image in the image that the biometric sensor obtains.

The performing of the user authentication may include, if it is determined, based on an external illuminance value, that an environment in which the image is obtained is an indoor environment in association with the specified condition, performing the user authentication based on the iris image.

The performing of the user authentication may include, if an environment in which the image is obtained is determined as an indoor environment (or is in an indoor environment) based on an external illuminance value and is a long distance environment in which a capture distance between a subject and the biometric sensor is not less than a specified distance in association with the specified condition, performing the user authentication based on the at least part of the face image and the iris image.

The performing of the user authentication may include, if it is determined, based on the obtained illuminance value, that an environment in which the image is obtained is an outdoor environment in association with the specified condition, performing the user authentication based on the at least part of the face image and the iris image.

The performing of the user authentication may include, if an environment in which the image is obtained is determined as an outdoor environment (or is in an outdoor environment) based on an external illuminance value and is a short distance environment in which a capture distance between a subject and the biometric sensor is less than a specified distance in association with the specified condition, performing the user authentication based on the at least part of the face image and the iris image.

The performing of the user authentication may include, if an environment in which the image is obtained is a long distance environment in which a distance between a subject and an infrared camera is not less than a specified distance, performing the user authentication based on the at least part of the face image and the iris image.

The performing of the user authentication may include determining that the environment in which the image is obtained is the long distance environment based on an iris size in the obtained iris image or a distance between two eyes in the obtained at least part of the face image.

The performing of the user authentication may include, if an environment in which the image is obtained is a short distance environment in which a distance between a subject and an infrared camera is less than a specified distance, performing the user authentication based on the iris image.

The performing of the user authentication may include, if the user authentication based on the iris image fails, performing the user authentication, based on the at least part of the face image and the iris image.

Figure 14:
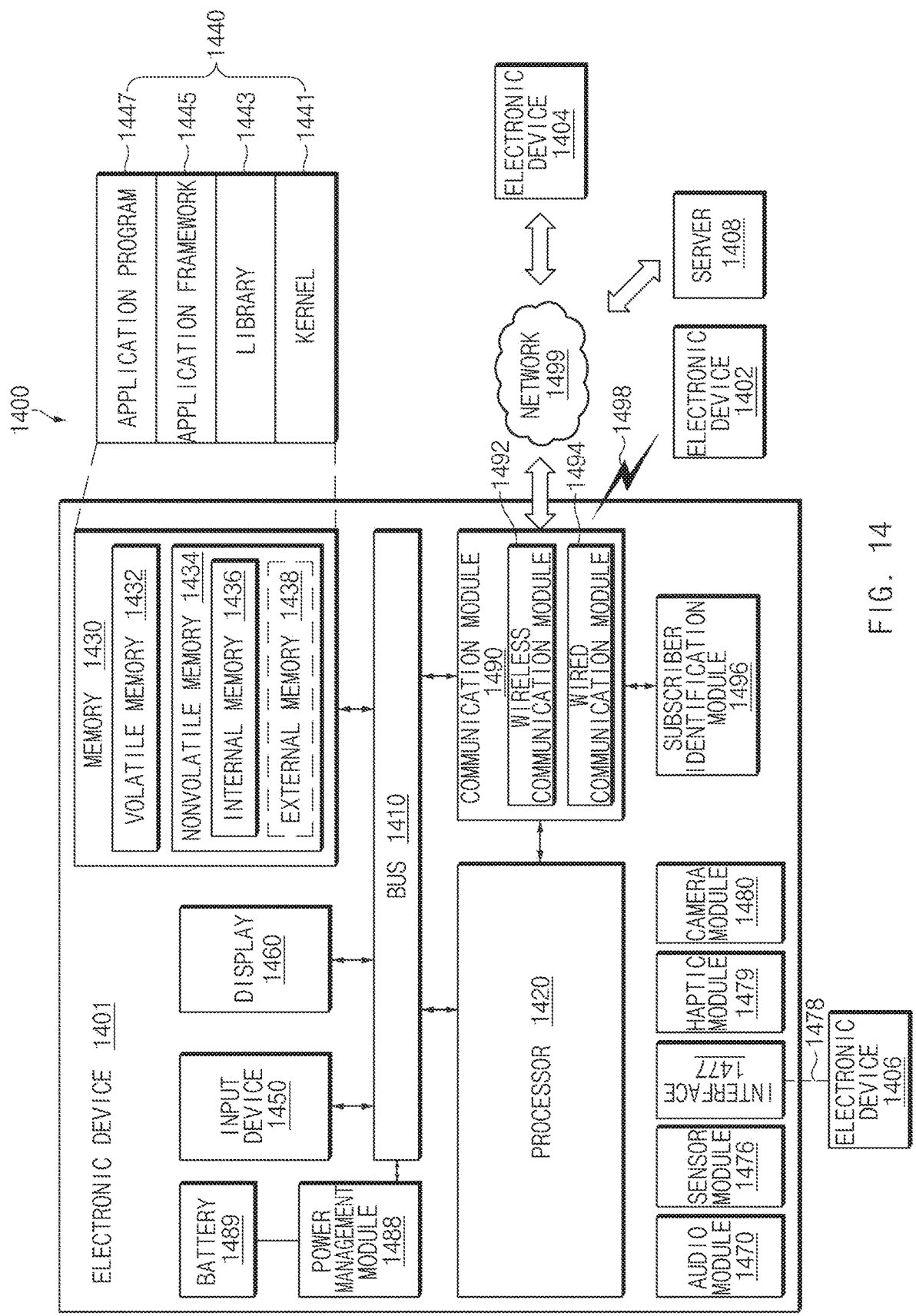
FIG. 14 is a block diagram of an electronic device in a network environment according to an embodiment of the disclosure.

FIG. 14 is a block diagram of an electronic device in a network environment according to various embodiments of the disclosure.

Referring to FIG. 14, under the network environment 1400, the electronic device 1401 (e.g., the electronic device 100) may communicate with an electronic device 1402 through local wireless communication 1498 or may communication with an electronic device 1404 or a server 1408 through a network 1499. The electronic device 1401 may communicate with the electronic device 1404 through the server 1408.

The electronic device 1401 may include a bus 1410, a processor 1420 (e.g., the processor 120) a memory 1430, an input device 1450 (e.g., a micro-phone or a mouse), a display 1460, an audio module 1470, a sensor module 1476, an interface 1477, a haptic module 1479, a camera module 1480, a power management module 1488, a battery 1489, a communication module 1490, and a subscriber identification module 1496. The electronic device 1401 may omit at least one (e.g., the display 1460 or the camera module 1480) of the above-described elements or may further include other element(s).

For example, the bus 1410 may interconnect the above-described elements 1420 to 1490 and may include a circuit for conveying signals (e.g., a control message or data) between the above-described elements. The processor 1420 may include one or more of a central processing unit (CPU), an application processor (AP), a graphic processing unit (GPU), an image signal processor (ISP) of a camera or a communication processor (CP). The processor 1420 may be implemented with a system on chip (SoC) or a system in package (SiP). For example, the processor 1420 may drive an operating system (OS) or an application to control at least one of another element (e.g., hardware or software element) connected to the processor 1420 and may process and compute various data. The processor 1420 may load an instruction or data, which is received from at least one of other elements (e.g., the communication module 1490), into a volatile memory 1432 to process the instruction or data and may store the process result data into a nonvolatile memory 1434.

The memory 1430 may include, for example, the volatile memory 1432 or the nonvolatile memory 1434. The volatile memory 1432 may include, for example, a random access memory (RAM) (e.g., a dynamic RAM (DRAM), a static RAM (SRAM), or a synchronous dynamic RAM (SDRAM)). The nonvolatile memory 1434 may include, for example, an one time programmable read-only memory (OTPROM), a programmable read-only memory (PROM), an erasable programmable read-only memory (EPROM), an electrically erasable programmable read-only memory (EEPROM), a mask ROM, a flash ROM, a flash memory, a hard disk drive, or a solid-state drive (SSD). In addition, the nonvolatile memory 1434 may be configured in the form of an internal memory 1436 or the form of an external memory 1438 which is available through connection only if necessary, according to the connection with the electronic device 1401. The external memory 1438 may further include a flash drive such as compact flash (CF), secure digital (SD), micro-SD, mini-SD, extreme digital (xD), a multimedia card (MMC), or a memory stick. The external memory 1438 may be operatively or physically connected with the electronic device 1401 in a wired manner (e.g., a cable or a universal serial bus (USB)) or a wireless (e.g., Bluetooth (BT)) manner.

The memory 1430 may store, for example, at least one different software element, such as an instruction or data associated with the program 1440, of the electronic device 1401. The program 1440 may include, for example, a kernel 1441, a library 1443, an application framework 1445 or an application program (interchangeably, "application") 1447.

The input device 1450 may include a microphone, a mouse, or a keyboard. According to an embodiment, the keyboard may include a keyboard physically connected or a keyboard virtually displayed through the display 1460.

The display 1460 may include a display, a hologram device or a projector, and a control circuit to control a relevant device. The screen may include, for example, a liquid crystal display (LCD), a LED display, an organic LED (OLED) display, a microelectromechanical systems (MEMS) display, or an electronic paper display. According to an embodiment, the display may be flexible, transparent, and/or wearable. The display may include a touch circuitry, which is able to detect a user's input such as a gesture input, a proximity input, or a hovering input or a pressure sensor (interchangeably, a force sensor) which is able to measure the intensity of the pressure by the touch. The touch circuit or the pressure sensor may be implemented integrally with the display or may be implemented with at least one sensor separately from the display. The hologram device may show a stereoscopic image in a space using interference of light. The projector may project light onto a screen to display an image. The screen may be located inside or outside the electronic device 1401.

The audio module 1470 may convert, for example, from a sound into an electrical signal or from an electrical signal into the sound. The audio module 1470 may obtain sound through the input device 1450 (e.g., a microphone) or may output sound through an output device (not illustrated) (e.g., a speaker or a receiver) included in the electronic device 1401, an external electronic device (e.g., the electronic device 1402 (e.g., a wireless speaker or a wireless headphone)) or an electronic device 1406 (e.g., a wired speaker or a wired headphone) connected with the electronic device 1401

The sensor module 1476 may measure or detect, for example, an internal operating state (e.g., power or temperature) or an external environment state (e.g., an altitude, a humidity, or brightness) of the electronic device 1401 to generate an electrical signal or a data value corresponding to the information of the measured state or the detected state. The sensor module 1476 may include at least one of a gesture sensor, a gyro sensor, a barometric pressure sensor, a magnetic sensor, an acceleration sensor, a grip sensor, a proximity sensor, a color sensor (e.g., an RGB sensor), an infrared sensor, a biometric sensor (e.g., an iris sensor, a fingerprint sensor, a heartbeat rate monitoring (HRM) sensor, an e-nose sensor, an electromyography (EMG) sensor, an electroencephalogram (EEG) sensor, an electrocardiogram (ECG) sensor, a temperature sensor, a humidity sensor, an illuminance sensor, or an UV sensor. The sensor module 1476 may further include a control circuit for controlling at least one or more sensors included therein. The sensor module 1476 may be controlled by using the processor 1420 or a processor (e.g., a sensor hub) separate from the processor 1420. In the case that the separate processor (e.g., a sensor hub) is used, while the processor 1420 is in a sleep state, the separate processor may operate without awakening the processor 1420 to control at least a portion of the operation or the state of the sensor module 1476.

The interface 1477 may include a high definition multimedia interface (HDMI), a USB, an optical interface, a recommended standard 232 (RS-232), a D-subminiature (D-sub), a mobile high-definition link (MHL) interface, a secure digital (SD) card/multi-media card (MMC) interface, or an audio interface. A connector 1478 may physically connect the electronic device 1401 and the electronic device 1406. The connector 1478 may include, for example, an USB connector, an SD card/MMC connector, or an audio connector (e.g., a headphone connector).

The haptic module 1479 may convert an electrical signal into mechanical stimulation (e.g., vibration or motion) or into electrical stimulation. For example, the haptic module 1479 may apply tactile or kinesthetic stimulation to a user. The haptic module 1479 may include, for example, a motor, a piezoelectric element, or an electric stimulator.

The camera module 1480 may capture, for example, a still image and a moving picture. The camera module 1480 may include at least one lens (e.g., a wide-angle lens and a telephoto lens, or a front lens and a rear lens), an image sensor, an ISP, or a flash (e.g., a light emitting diode or a xenon lamp).

The power management module 1488, which manages the power of the electronic device 1401, may constitute at least a portion of a power management integrated circuit (PMIC).

The battery 1489 may include a primary cell, a secondary cell, or a fuel cell and may be recharged by an external power source to supply power at least one element of the electronic device 1401.

The communication module 1490 may establish a communication channel between the electronic device 1401 and an external device (e.g., the first external electronic device 1402, the second external electronic device 1404, or the server 1408). The communication module 1490 may support wired communication or wireless communication through the established communication channel. According to an embodiment, the communication module 1490 may include a wireless communication module 1492 or a wired communication module 1494. The communication module 1490 may communicate with the external device (e.g., the first external electronic device 1402, the second external electronic device 1404 or the server 1408) through a first network 1498 (e.g. a wireless local area network (WLAN) such as BT or infrared data association (IrDA)) or a second network 1499 (e.g., a wireless wide area network such as a cellular network) through a relevant module among the wireless communication module 1492 or the wired communication module 1494.

The wireless communication module 1492 may support, for example, cellular communication, local wireless communication, GNSS communication. The cellular communication may include, for example, long-term evolution (LTE), LTE Advance (LTE-A), code division multiple access (CMA), wideband CDMA (WCDMA), universal mobile telecommunications system (UNITS), wireless broadband (WiBro), or global system for mobile communications (GSM). The local wireless communication may include wireless fidelity (Wi-Fi), WiFi Direct, light fidelity, BT, Bluetooth low energy (BLE), Zigbee, near field communication (NFC), magnetic secure transmission (MST), radio frequency (RF), or a body area network (BAN). The GNSS may include at least one of a global positioning system (GPS), a global navigation satellite system (Glonass), Beidou Navigation Satellite System (Beidou), the European global satellite-based navigation system (Galileo), or the like. In the disclosure, "GPS" and "GNSS" may be interchangeably used.

According to an embodiment, when the wireless communication module 1492 supports cellar communication, the wireless communication module 1492 may, for example, identify or authenticate the electronic device 1401 within a communication network using the subscriber identification module (e.g., a SIM card) 1496. According to an embodiment, the wireless communication module 1492 may include a CP separate from the processor 2820 (e.g., an AP. In this case, the CP may perform at least a portion of functions associated with at least one of elements 1410 to 1496 of the electronic device 1401 in substitute for the processor 1420 when the processor 1420 is in an inactive (sleep) state, and together with the processor 1420 when the processor 1420 is in an active state. The wireless communication module 1492 may include a plurality of communication modules, each supporting only a relevant communication scheme among cellular communication, short-range wireless communication, or a GNSS communication scheme.

The wired communication module 1494 may include, for example, include a local area network (LAN) service, a power line communication, or a plain old telephone service (POTS).

For example, the first network 1498 may employ, for example, Wi-Fi direct or BT for transmitting or receiving instructions or data through wireless direct connection between the electronic device 1401 and the first external electronic device 1402. The second network 1499 may include a telecommunication network (e.g., a computer network such as a LAN or a WAN, the Internet or a telephone network) for transmitting or receiving instructions or data between the electronic device 1401 and the second electronic device 1404.

The instructions or the data may be transmitted or received between the electronic device 1401 and the second external electronic device 1404 through the server 1408 connected with the second network. Each of the external first and second external electronic devices 1402 and 1404 may be a device of which the type is different from or the same as that of the electronic device 1401. All or a part of operations that the electronic device 1401 will perform may be executed by another or a plurality of electronic devices (e.g., the electronic devices 1402 and 1404 or the server 1408). In the case that the electronic device 1401 executes any function or service automatically or in response to a request, the electronic device 1401 may not perform the function or the service internally, but may alternatively or additionally transmit requests for at least a part of a function associated with the electronic device 1401 to any other device (e.g., the electronic device 1402 or 1404 or the server 1408). The other electronic device (e.g., the electronic device 1402 or 1404 or the server 1408) may execute the requested function or additional function and may transmit the execution result to the electronic device 1401. The electronic device 1401 may provide the requested function or service using the received result or may additionally process the received result to provide the requested function or service. To this end, for example, cloud computing, distributed computing, or client-server computing may be used.

Various embodiments of the disclosure and terms used herein are not intended to limit the technologies described in the present disclosure to specific embodiments, and it should be understood that the embodiments and the terms include modification, equivalent, and/or alternative on the corresponding embodiments described herein. With regard to description of drawings, similar elements may be marked by similar reference numerals. The terms of a singular form may include plural forms unless otherwise specified. In the disclosure disclosed herein, the expressions "A or B", "at least one of A and/or B", "at least one of A and/or B", "A, B, or C", or "at least one of A, B, and/or C", and the like used herein may include any and all combinations of one or more of the associated listed items. Expressions such as "first," or "second," and the like, may express their elements regardless of their priority or importance and may be used to distinguish one element from another element but is not limited to these components. When an (e.g., first) element is referred to as being "(operatively or communicatively) coupled with/to" or "connected to" another (e.g., second) element, it may be directly coupled with/to or connected to the other element or an intervening element (e.g., a third element) may be present.

According to the situation, the expression "adapted to or configured to" used herein may be interchangeably used as, for example, the expression "suitable for", "having the capacity to", "changed to", "made to", "capable of" or "designed to". The expression "a device configured to" may mean that the device is "capable of" operating together with another device or other components. For example, a "processor configured to (or set to) perform A, B, and C" may mean a dedicated processor (e.g., an embedded processor) for performing corresponding operations or a generic-purpose processor (e.g., a CPU or an AP) which performs corresponding operations by executing one or more software programs which are stored in a memory device (e.g., the memory 830).

The term "module" used herein may include a unit, which is implemented with hardware, software, or firmware, and may be interchangeably used with the terms "logic", "logical block", "component", "circuit", or the like. The "module" may be a minimum unit of an integrated component or a part thereof or may be a minimum unit for performing one or more functions or a part thereof. The "module" may be implemented mechanically or electronically and may include, for example, an application-specific IC (ASIC) chip, a field-programmable gate array (FPGA), and a programmable-logic device for performing some operations, which are known or will be developed.

According to various embodiments of the disclosure, at least a part of an apparatus (e.g., modules or functions thereof) or a method (e.g., operations) may be, for example, implemented by instructions stored in a computer-readable storage media (e.g., the memory 830) in the form of a program module. The instruction, when executed by a processor (e.g., a processor 820), may cause the processor to perform a function corresponding to the instruction. The computer-readable recording medium may include a hard disk, a floppy disk, a magnetic media (e.g., a magnetic tape), an optical media (e.g., a compact disc read only memory (CD-ROM) and a DVD, a magneto-optical media (e.g., a floptical disk)), an embedded memory, and the like. The one or more instructions may contain a code made by a compiler or codes executable by an interpreter.

Each element (e.g., a module or a program module) may be composed of single entity or a plurality of entities, a part of the above-described sub-elements may be omitted or may further include other elements. Alternatively or additionally, after being integrated in one entity, some elements (e.g., a module or a program module) may identically or similarly perform the function executed by each corresponding element before integration. Operations executed by modules, program modules, or other elements may be executed by a successive method, a parallel method, a repeated method, or a heuristic method, or at least one part of operations may be executed in different sequences or omitted. Alternatively, other operations may be added.

While the present disclosure has been shown and described with reference to various embodiments thereof, it will be understood by those skilled in the art that various changes in form and details may be made therein without departing from the spirit and scope of the present disclosure as defined by the appended claims and their equivalents.

What is claimed is:

1. An electronic device comprising:
    an illuminance sensor;
    a biometric sensor including:
        a light emitting element, and
        an infrared camera;
    a memory; and
    a processor operatively coupled to the biometric sensor and the memory,
    wherein the processor is configured to:
        determine, prior to performing user authentication in response to an authentication request, whether an external illuminance value, obtained from the illuminance sensor, meets a specified condition,
        when the specified condition is satisfied, perform the user authentication based on at least a portion of a face image and an iris image obtained by the biometric sensor,
        when the specified condition is not satisfied, perform the user authentication based on the iris image obtained by the biometric sensor, and when the external illuminance value corresponds to an indoor environment and a capture distance between a subject and the biometric sensor corresponds to a first distance in association with the specified condition, perform the user authentication based on the at least the portion of the face image and the iris image.

2. The electronic device of claim 1, wherein the processor is further configured to:
when the external illuminance value corresponds to an outdoor environment in association with the specified condition, perform the user authentication based on the at least the portion of the face image and the iris image.

3. The electronic device of claim 1, wherein the processor is further configured to:
when the external illuminance value corresponds to an outdoor environment and the capture distance between the subject and the biometric sensor corresponds to a second distance in association with the specified condition, perform the user authentication based on the at least the portion of the face image and the iris image.

4. The electronic device of claim 1, wherein the processor is further configured to:
when a distance between a subject and the infrared camera corresponds to the first distance in association with the specified condition, perform the user authentication based on the at least the portion of the face image and the iris image.

5. The electronic device of claim 4, wherein the processor is further configured to:
determine the first distance based on at least one of an iris size in the iris image or a distance between two eyes in the at least the portion of the face image, in association with the specified condition.

6. The electronic device of claim 1, wherein the processor is further configured to:
when a distance between a subject and the infrared camera corresponds to a second distance in association with the specified condition, perform the user authentication based on the iris image.

7. The electronic device of claim 1, wherein the processor is further configured to:
determine the at least the portion of the face image based on the external illuminance value and obtain reference data corresponding to the determined at least the portion of the face image.

8. The electronic device of claim 1, wherein the processor is further configured to:
when the specified condition is not satisfied and the user authentication based on the iris image fails, perform the user authentication, based on the at least the portion of the face image and the iris image.

9. The electronic device of claim 1, further comprising: a display,
wherein the processor is further configured to display a guide interface on the display to request a user to move a face in a specified direction.

10. The electronic device of claim 1, wherein the processor is further configured to at least one of:
control a light emitting element to be emitting light of an infrared wavelength band; or
control an infrared camera to be obtaining an image based on the light of the infrared wavelength band.

11. An iris-based authentication method, the method comprising:
emitting light of an infrared wavelength band and obtaining an image based on the light of the infrared wavelength band of a biometric sensor;
determining, prior to performing user authentication in response to an authentication request, whether an external illuminance value, obtained from an illuminance sensor, meets a specified condition;
when the specified condition is satisfied, performing the user authentication based on at least a portion of a face image and an iris image obtained by the biometric sensor;
when the specified condition is not satisfied, performing the user authentication based on the iris image obtained by the biometric sensor; and
when the external illuminance value corresponds to an indoor environment and a capture distance between a subject and the biometric sensor corresponds to a first distance in association with the specified condition, performing the user authentication based on the at least the portion of the face image and the iris image.

12. The method of claim 11, wherein the performing of the user authentication includes:
when the external illuminance value corresponds to an outdoor environment in association with the specified condition, performing the user authentication based on the at least the portion of the face image and the iris image.

13. The method of claim 11, wherein the performing of the user authentication includes:
when the external illuminance value corresponds to an outdoor environment and the capture distance between the subject and the biometric sensor corresponds to a second distance in association with the specified condition, performing the user authentication based on the at least the portion of the face image and the iris image.

14. The method of claim 11, wherein the performing of the user authentication includes:
when a distance between a subject and an infrared camera corresponds to the first distance in association with the specified condition, performing the user authentication based on the at least the portion of the face image and the iris image.

15. The method of claim 14, wherein the performing of the user authentication includes:
determining that an environment in which the image is obtained is a long distance environment based on at least one of an iris size in the iris image or a distance between two eyes in the at least the portion of the face image.

16. The method of claim 11, wherein the performing of the user authentication includes:
when a distance between a subject and an infrared camera corresponds to a second distance in association with the specified condition, performing the user authentication based on the iris image; or
when the specified condition is not satisfied and when the user authentication based on the iris image fails, performing the user authentication, based on the at least the portion of the face image and the iris image.

17. The method of claim 11, further comprising:
displaying a guide interface on a display to request a user to move a face in a specified direction.

18. The method of claim 11, further comprising:
displaying a message, on a display, instructing a user to adjust an environment for obtaining the image based on the light of the infrared wavelength band.

19. The method of claim 11, wherein the specified condition comprises an illuminance value corresponding to an outdoor environment.

\* \* \* \* \*